| (12) | United States Patent | (10) Patent No.: | US 12,205,683 B2 |
|---|---|---|---|
| | Aykol et al. | (45) Date of Patent: | *Jan. 21, 2025 |

(54) METHODS FOR PREDICTING LIKELIHOOD OF SUCCESSFUL EXPERIMENTAL SYNTHESIS OF COMPUTER-GENERATED MATERIALS BY COMBINING NETWORK ANALYSIS AND MACHINE LEARNING

(71) Applicant: TOYOTA RESEARCH INSTITUTE, INC., Los Altos, CA (US)

(72) Inventors: Muratahan Aykol, Santa Clara, CA (US); Santosh Karthik Suram, Mountain View, CA (US); Linda Hung, Mountain View, CA (US); Patrick Kenichi Herring, Mountain View, CA (US)

(73) Assignee: TOYOTA RESEARCH INSTITUTE, INC., Los Altos, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 18/147,471

(22) Filed: Dec. 28, 2022

(65) Prior Publication Data

US 2023/0135041 A1 May 4, 2023

Related U.S. Application Data

(63) Continuation of application No. 16/004,232, filed on Jun. 8, 2018, now Pat. No. 11,580,431.

(51) Int. Cl.
*G16C 60/00* (2019.01)
*G06F 18/241* (2023.01)
(Continued)

(52) U.S. Cl.
CPC ............... *G16C 60/00* (2019.02); *G06N 7/01* (2023.01); *G06N 20/00* (2019.01); *G16C 20/10* (2019.02); *G16C 20/70* (2019.02); *G06F 18/241* (2023.01)

(58) Field of Classification Search
CPC ........ G16C 60/00; G16C 20/10; G16C 20/70; G06N 20/00; G06N 7/01
See application file for complete search history.

(56) References Cited

U.S. PATENT DOCUMENTS

2015/0025931 A1* 1/2015 Li ..................... G06Q 10/0633 705/7.27

OTHER PUBLICATIONS

Kim, Edward, et al. "Materials synthesis insights from scientific literature via text extraction and machine learning." Chemistry of Materials 29.21 (2017): 9436-9444. (Year: 2017).*

* cited by examiner

*Primary Examiner* — Eric Nilsson
(74) *Attorney, Agent, or Firm* — SHEPPARD, MULLIN, RICHTER & HAMPTON LLP; Daniel N. Yannuzzi

(57) ABSTRACT

One aspect of the disclosure relates to systems and methods for determining probabilities of successful synthesis of materials in the real world at one or more points in time. The probabilities of successful synthesis of materials in the real world at one or more points in time can be determined by representing the materials and their pre-defined relationships respectively as nodes and edges in a network form, and computation of the parameters of the nodes in the network as input to a classification model for successful synthesis. The classification model being configured to determine probabilities of successful synthesis of materials in the real world at one or more points in time.

12 Claims, 11 Drawing Sheets

(51) Int. Cl.
*G06N 7/01* (2023.01)
*G06N 20/00* (2019.01)
*G16C 20/10* (2019.01)
*G16C 20/70* (2019.01)

| Previously Synthesized Material 400 | Discovery Time 500 |
|---|---|
| Material 401 | Material 401 : Time 501 |
| Material 402 | Material 404 : Time 502 |
| Material 403 | Material 405 : Time 503 |
| Material 404 | Material 404 : Time 504 |
| Material 405 | Material 405 : Time 505 |
| Material 406 | Material 406 : Time 506 |
| Material 407 | Material 407 : Time 507 |
| Material 408 | Material 408 : Time 508 |
| Material 409 | Material 409 : Time 509 |
| Material 410 | Material 410 : Time 510 |
| ⋮ | ⋮ |
| Material i | Material i : Time J |

FIG. 4

METHODS FOR PREDICTING LIKELIHOOD OF SUCCESSFUL EXPERIMENTAL SYNTHESIS OF COMPUTER-GENERATED MATERIALS BY COMBINING NETWORK ANALYSIS AND MACHINE LEARNING

CROSS-REFERENCE TO RELATED APPLICATIONS

This application is a continuation of and claims the benefit of U.S. patent application Ser. No. 16/004,232 filed Jun. 8, 2018, which is hereby incorporated herein by reference in its entirety for all purposes.

TECHNICAL FIELD

The present disclosure relates to predicting probabilities of materials being synthesized in the real world at one or more points in time.

DESCRIPTION OF RELATED ART

Attempting to synthesize a new material can be costly. Synthesizing the new material includes a chance of failure. Synthesizing a new material with a low chance of success may increase the cost of the new material.

BRIEF SUMMARY OF THE DISCLOSURE

One aspect of the disclosure relates to systems and methods for determining probabilities of successful synthesis of materials in the real world at one or more points in time. The materials may be materials not yet synthesized (e.g., unsynthesized) in the real world and/or other materials. The unsynthesized materials may be one or more of a hypothetical material, computer-generated hypothetical material, theoretical materials, and/or other materials. The one or more points in time may be one or more discrete points in time. The discrete points in time may include points in time in the past and in the future. The discrete points in time may be specified in months, years, decades, and/or other time measurements.

The probabilities may be determined by a classifier model. The classifier model may be obtained by training the classifier model. The classifier model may be trained based on a set of previously synthesized materials and time of first synthesis of the individual previously synthesized materials. The set of previously synthesized materials may form a network. The network may change (or evolve) based on a given point in time the network represents. The network at a given point in time may include nodes representing the individual previously synthesized materials that were synthesized by the given point in time. Network parameter information may be determined based on the network. The network parameter information may define sets of parameter values for the individual nodes in the network and/or the individual previously synthesized materials and/or other information at discrete points in time of a period of time. Status of discovery information indicating whether the individual previously synthesized materials that were synthesized by the individual discrete points in time may be determined. The classifier model may be trained based on the network parameter information, status of discovery information, and/or other information. The classifier model may be configured to generate values specifying the probabilities of successful synthesis of materials in the real world at the individual discrete points in time. The values specifying the probabilities of successful synthesis of materials in the real world at the individual discrete points in time may be presented on an interface on a computing platform. A user may manipulate the interface to view the information defining the values specifying the probabilities of successful synthesis of materials in the real world at the individual discrete points in time.

In some implementations, a system configured to determine probabilities of successful synthesis of materials in the real world at one or more points in time may include one or more servers, one or more computing platforms, one or more external resources, and/or other components. Users may access the system via the computing platforms, and/or other devices. In some implementations, the server(s) may include one or more of electronic storage, one or more physical processors, and/or other components. In some implementations, the one or more physical processors may be configured by machine-readable instructions. Executing the machine-readable instructions may cause the one or more physical processors to determine the probability of successful synthesis of materials in the real world at one or more points in time. The machine-readable instructions may include one or more computer program components. The one or more computer program components may include one or more of an information component, a determination component, a training component, a prediction component, a presentation component, and/or other components.

The electronic storage may be configured to store material network information and/or other information. The material network information may define a network for a set of materials and/or other information. The set of materials of the network may be a set of previously synthesized and/or unsynthesized materials. The material network information may include node information, edge information, discovery information, and/or other information. The node information may characterize the materials represented by nodes in the network. The edge information may characterize the connections between the materials in the network based on shared components between the materials (e.g., same chemical structures) or based on thermodynamic quantities of materials (e.g., co-existence information from phase diagrams or energy-composition network, also known as the energy convex-hull, formed using the formation energies of materials). The edge information may characterize the connections represented by edges in the network. The discovery information may define when the individual previously synthesized materials of the set of previously synthesized materials were first synthesized in the real world.

The information component may be configured to obtain the material network information and/or other information. The information component may be configured to obtain the material network information from the electronic storage, the external resources, and/or other storage locations. The information component may be configured to obtain publication information and/or other information. The publication information may be used to define when the individual previously synthesized materials were first synthesized in the real world.

The determination component may be configured to obtain network parameter information and/or information. The determination component may be configured to determine the network parameter information based on the material network information and/or other information. The network parameter information may specify sets of parameter values for the individual nodes in the network and/or individual previously synthesized materials at discrete points in time over a period of time. The sets of parameter values for an individual node and/or individual previously synthesized material at the discrete points in time over a period of time may include parameter values at the individual discrete points in time. The network may change (or evolve) over the discrete points in time of the period of time. The network at given discrete points in time of the period of time may include only nodes representing individual previously synthesized materials that were synthesized in the real world by the given discrete points in time. The determination component may determine the sets of parameter values for the individual nodes and/or individual previously synthesized materials based on the network that changes (or evolves) over the discrete points in time of the period of time.

The training component may be configured to train a classifier model. The training component may train the classifier model based on the individual previously synthesized materials, the time of first synthesis of the individual previously synthesized materials, and/or other information. The training component may train the classifier model based on the network characterizing the set of previously synthesized materials. The training component may train the classifier model using some of the previously synthesized materials of the set of previously synthesized materials, and test the classifier model with the remaining previously synthesized materials of the set of previously synthesized materials. The training component may train the classifier model using one or more machine learning, training techniques, and/or other techniques. The trained classifier model may generate probabilities for materials being successfully synthesized in the real world at the individual discrete points in time.

The prediction component may be configured to determine probability information and/or other information. The probability information may define one or more values specifying probabilities of materials will be successfully synthesized in the real world at the individual discrete points in time. The prediction component may be configured to obtain the trained classifier model and/or other information. The prediction component may be configured to obtain material information defining the materials. The prediction component may apply the classifier model to the material information and/or information associated with the material to generate the one or more values specifying probabilities of materials will be successfully synthesized in the real world at the individual discrete points in time.

The presentation component may be configured to effectuate presentation of an interface and/or other information. The presentation component may be configured to effectuate presentation of the interface and/or other information on the computing platforms and/or other devices. The interface may include a virtual space, one or more virtual objects, and/or other information. The interface may present the probability information and/or other information through the one or more virtual objects positioned within a topography of the virtual space. In some implementations, the presentation component may be configured to obtain user inputs defining user instructions from one or more users. The user instructions may instruct the presentation component to effectuate presentation of specific information on the interface.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description and are not intended as a definition of the limits of the invention. As used in the specification and in the claims, the singular form of "a," "an," and "the" include plural referents unless the context clearly dictates otherwise.

BRIEF DESCRIPTION OF THE DRAWINGS

FIG. 4 illustrates an example of the information defined by the material network information, in accordance with one or more implementations.

DETAILED DESCRIPTION

Figure 1:
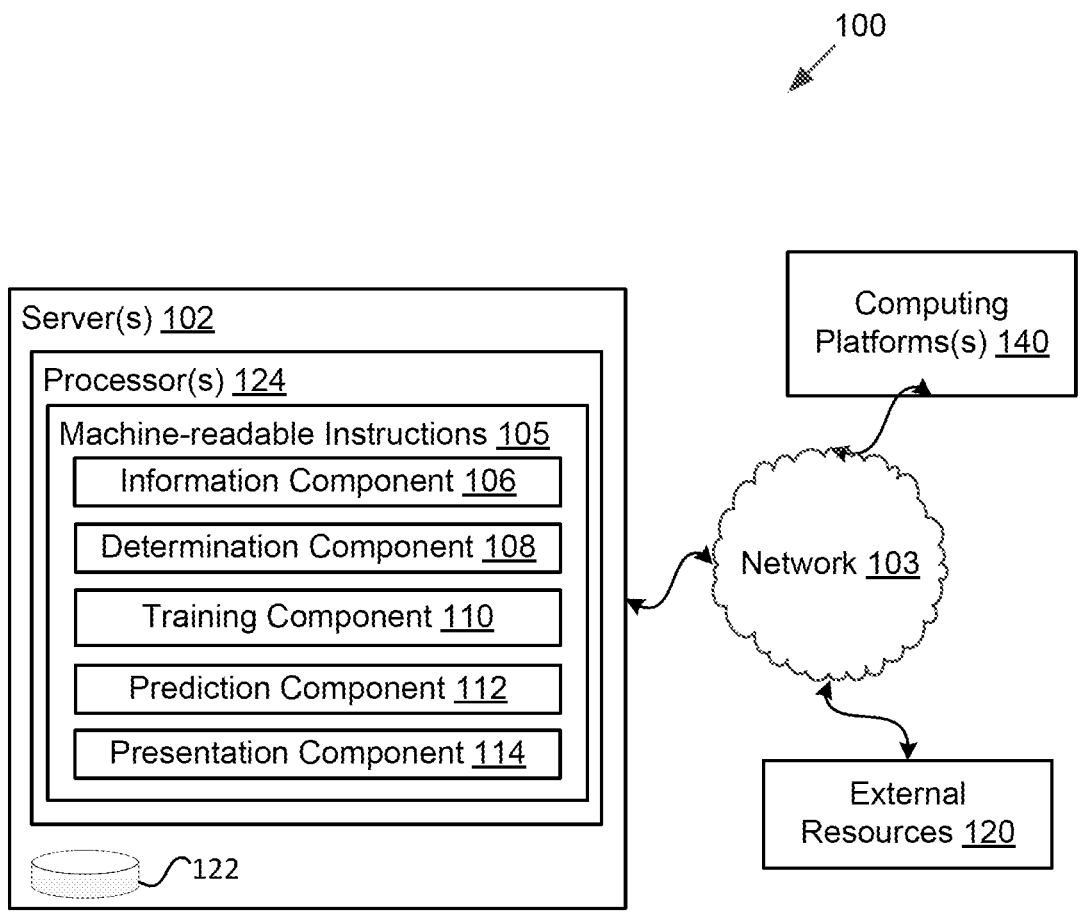
FIG. 1 illustrates a system for determining a probability of successful synthesis of a material as a function of time, in accordance with one or more implementations.

FIG. 1 illustrates a system 100 configured to determine probabilities of successful synthesis of materials in the real world at one or more points in time. System 100 may be configured to train a classifier model for determining the probabilities. System 100 may be configured to apply the trained classifier model to determine the probabilities. The materials may be materials not yet synthesized (e.g., unsynthesized) and/or already synthesized in the real world.

In some implementations, system 100 configured to determine probabilities of successful synthesis of materials in the real world at one or more points in time may include one or more servers 102, one or more computing platforms 140, one or more external resources 120, and/or other components. Users may access system 100 via the computing platform(s) 140 and/or other devices. In some implementations, server(s) 102 may include one or more of electronic storage 122, one or more physical processors 124, and/or other components. In some implementations, the one or more physical processors 124 may be configured by machine-readable instructions 105. Executing machine-readable instructions 105 may cause processor(s) 124 to determine the probability of successful synthesis of materials in the real world at one or more points in time. Machine-readable instructions 105 may include one or more computer program components. The one or more computer program components may include one or more of an information component 106, a determination component 108, a training component 110, a prediction component 112, a presentation component 114, and/or other components.

Computing platform(s) 140 may be one or more of a mobile computing device (such as one or more of a smartphone, smartwatch, etc.), a personal computer, a network of computers, a wearable computing device (such as a head-mounted computing device), a game console, and/or other computing platforms. In some implementations, computing platform(s) 140 may be one or more of a quantum computing platform, biocomputing platforms, and/or other computing platforms. Computing platform(s) 140 may include one or more of one or more input devices, one or more displays, one or more sensors, one or more audio output devices, and/or other components. It is noted that computing platform(s) 140 may represent an individual computing platform and/or more than one computing platform that may be similarly configured as described herein.

The input devices of computing platform(s) 140 may include one or more of a computer mouse, a keyboard, a game controller, a touch-enabled input device, and/or other input devices. The input devices may be removably coupled to computing platform(s) 140. The input devices may be integrated with computing platform(s) 140.

The touch-enabled input device may be a touch screen and/or other devices. The touch screen may include one or more of a resistive touchscreen, a capacitive touchscreen, a surface acoustic wave touchscreen, an infrared touchscreen, an optical imaging touchscreen, an acoustic pulse recognition touchscreen, and/or other touchscreens. The touch-enabled input device may be configured to generate output signals conveying touch gesture information defining touch gesture inputs of the user.

The displays may be a device configured to effectuate presentation of visual content. The displays include one or more of a touch-enabled display (e.g., the touchscreen), an LCD display, a LED display, an OLED display, a projector, and/or other displays. In some implementations, the display may be a video projector and/or other devices.

The sensors of computing platform(s) 140 may include one or more image sensors, audio sensors, and/or other sensors. The audio output devices for computing platform(s) 140 may be one or more of a speaker, a headphone, an earbud, and/or other audio output devices.

In some implementations, an image sensor may be configured to generate output signals conveying visual information and/or other information. The visual information may define visual content within a field of view of the image sensor and/or other content. The visual content may include depictions of real-world objects and/or surfaces. The visual content may be in the form of one or more of images, videos, and/or other visual information. The field of view of the image sensor may be a function of a position and an orientation of a computing platform. In some implementations, an image sensor may comprise one or more of a photosensor array (e.g., an array of photosites), a charge-coupled device sensor, an active pixel sensor, a complementary metal-oxide semiconductor sensor, an N-type metal-oxide-semiconductor sensor, and/or other devices.

In some implementations, an audio sensor may be configured to generate output signals conveying audio information and/or other information. The audio information may define audio from a user of the audio sensor (e.g., utterances of the user), audio around the user (such as ambient audio), and/or other information. In some implementations, an audio sensor may include one or more of a microphone, a micro-electro-mechanical microphone, and/or other devices.

Electronic storage 122 may be configured to store material network information and/or other information. The material network information may define sets of materials and/or other information. Some of the materials of a set of materials may have at least one shared feature. A shared feature may be a common chemical structure and/or element. The materials may also be chemicals. In some implementations, a material can be, at the minimum, defined as a unique arrangement of one more kinds of element atoms from the periodic table in a given crystal structure at a given composition, and/or with other information regarding its structure, morphology and other features. The set of materials may be previously synthesized materials and/or synthesized materials. The materials may include one or more stable materials, unstable materials, metastable materials, and/or other materials. The materials may be defined based on its crystalline information, including a bulk crystalline level and/or other information. The material network information may characterize the sets of materials with a network and/or other information. The material network information may characterize a set of previously synthesized materials with a network and/or other information.

In some implementations, the material network information may be obtained from high-throughput density function theory databases. The high-throughput density function theory databases may include one or more of Open Quantum Materials Database, Materials Project Database, AFLOW-LIB Database, and/or other databases. In some implementations, the material network information may be generated based on density functional theory calculation and/or other techniques. The network may be a thermodynamic network of materials. For example, the network may be a thermodynamic network of stable materials (e.g., co-existence information from the material phase diagrams or the network obtained by taking the convex-hull of the energy—composition space, where the materials are the nodes and the tie-lines formed between materials are the edges).

The material network information may include node information, edge information, discovery information, and/or other information. The node information, edge information, and/or other information may characterize the sets of materials (such as the set of previously synthesized materials) in a network. The node information may characterize the materials (such as the previously synthesized materials) represented by nodes in the network. Individual nodes in the network may represent individual materials of the set of materials.

In some implementations, the material network information may characterize the materials (such as the previously synthesized materials) by a dataset and/or other information. The network may be characterized by the dataset. The dataset may include one or more values. The one or more values of the dataset may characterize the materials. The dataset may be represented by one or more matrixes and/or other representation. The one or more matrixes may include one or more dimensions and/or other information. The dataset may characterize the node information, edge information, discovery information, and/or other information. The dataset may be used to train one or more classifier models, algorithms, and/or other models.

The edge information may characterize the connections between the materials (such as the previously synthesized materials) in the network. The edge information may characterize the connections represented by edges in the network. The connections between the materials in the network may be based on one or more shared components and/or relationships between the materials. The connections between the materials in the network may indicate shared components and/or a relationship between the materials.

The shared components between the materials may include one or more of a shared chemical structure, chemical-relevance, and/or other common elements. The relationships between the materials may include one or more of a shared inventor, shared time of discovery, shared location of discovery, shared chemical effect, shared method of discovery, shared time of discovery, and/or other relationships. In some other implementations, the relationships between materials may include thermodynamic co-existence information that may be obtained from the material phase diagrams, such as the convex-hull of the free energy—composition space of materials obtained from high-throughput density functional theory calculations of materials. In some implementations, some of the materials may share components and/or be related to some of the materials. In some implementations, individual ones of the materials may share components and/or be related to individual ones of the materials in the network.

The discovery information may specify when the individual previously synthesized materials of the set of previously synthesized materials were first synthesized in the real world. The discovery information may specify points in time the set of previously synthesized materials were first synthesized in the real world. The discovery information may specify the year the individual previously synthesized materials of the set of previously synthesized materials were first synthesized in the real world. The discovery information may specify the month of the year the individual previously synthesized materials of the set of previously synthesized materials were first synthesized in the real world. The discovery information may specify the day of the month of the year the individual previously synthesized materials of the set of previously synthesized materials were first synthesized in the real world. The discovery information may specify the time of the day of the month of the year the individual previously synthesized materials of the set of previously synthesized materials were first synthesized in the real world. Individual previously synthesized materials of the set of previously synthesized materials may be first synthesized in the real world at different points in time and/or at the same point in time.

In some implementations, the discovery information may specify an approximate time the individual previously synthesized materials of the set of previously synthesized materials were first synthesized in the real world. The discovery information may specify an approximate decade the individual previously synthesized materials of the set of previously synthesized materials were first synthesized in the real world. The approximate time the individual previously synthesized materials of the set of previously synthesized materials were first synthesized in the real world may be determined by rounding the point in time the individual previously synthesized materials of the set of previously synthesized materials were first synthesized in the real world. For example, the point in time the individual previously synthesized materials of the set of previously synthesized materials were first synthesized in the real world may be rounded to the nearest month of a year, the nearest year, the nearest decade, and/or other times.

In some implementations, when the individual previously synthesized materials of the set of previously synthesized materials were synthesized in the real world may be specified by one or more publications and/or other sources. The publications may include one or more of a magazine, journal, records, crystallographic database, abstract database, and/or other publications and/or databases. The publication dates of the publications may specify the points in time and/or approximate points in time the individual previously synthesized materials of the set of previously synthesized materials were first synthesized in the real world.

In some implementations, electronic storage 122 may be configured to store one or more classifier models, information defining the classifier models, and/or other information.

Information component 106 may be configured to obtain the material network information and/or other information. Information component 106 may be configured to obtain the material network information including the node information, edge information, discovery information, and/or other information. The information component may be configured to obtain the material network information from electronic storage 122, external resources 120, and/or other storage locations.

In some implementations, information component 106 may be configured to generate and/or determine the material network information and/or other information. Information component 106 may be configured to generate and/or determine the material network information, including the node information, the edge information, the discovery information, and/or other information. Information component 106 may be configured to generate and/or determine the material network information based on the node information, the edge information, the discovery information, and/or other information.

Information component 106 may be configured to obtain information defining the sets of materials, including the set of previously synthesized materials, and/or other information. Some of the previously synthesized materials of the set of previously synthesized materials may have at least one shared feature. Information component 106 may be configured to obtain the information defining the set of previously synthesized materials and/or other information from electronic storage 122, external resources 120, and/or other databases and/or sources. In some implementations, information component 106 may be configured to obtain information defining the set of previously synthesized materials and/or other information from the high-throughput density function theory databases and/or other databases. Information component 106 may be configured to obtain information defining the set of previously synthesized materials and/or other information from the one or more of the Open Quantum Materials Database, Materials Project Database, AFLOWLIB Database, and/or other databases.

The information defining the set of previously synthesized materials may specify a list of the previously synthesized materials that were synthesized in the real world by a given point in time and/or over a period of time. For example, the information defining the set of previously synthesized materials may specify a list of the previously synthesized materials that were synthesized in the real world by the year 2000, the year 2005, the year 2010, the year 2015, and/or other points in time. The list of the previously synthesized materials that were synthesized in the real world by the year 2000 may include previously synthesized materials that were synthesized in the real world before 2000.

The information defining the set of previously synthesized materials may specify a list of the previously synthesized materials that were synthesized in the real world after a given point in time and/or over a period of time. For example, the information defining the set of previously synthesized materials may specify a list of the previously synthesized materials that were synthesized in the real world after the year 2000, the year 2005, the year 2010, the year 2015, and/or other points in time. The list of the previously synthesized materials that were synthesized in the real world after the year 2000 may include previously synthesized materials that were synthesized in the real world after 2000.

The set of previously synthesized materials may be represented by a dataset and/or other representation. The dataset may include one or more values characterizing the individual previously synthesized materials of the set of previously synthesized materials. The dataset may be represented by a matrix with one or more values. The one or more values of the matrix may characterize the individual previously synthesized materials of the set of previously synthesized materials.

In some implementations, the set of the previously synthesized materials that were synthesized in the real world by or after a given point in time may range between 100 to 100,000 previously synthesized materials that were synthesized in the real world by the given point in time and/or other points in time. In some implementations, the set of the previously synthesized materials that were synthesized in the real world by or after a given point in time may range between 1000 to 10,000 previously synthesized materials that were synthesized in the real world by the given point in time and/or other points in time. In some implementations, the set of the previously synthesized materials that were synthesized in the real world by or after a given point in time may range between 10,000 to 100,000 previously synthesized materials that were synthesized in the real world by the given point in time and/or other points in time. In some implementations, the set of the previously synthesized materials that were synthesized in the real world by or after a given point in time may range between 10,000 to 50,000 previously synthesized materials that were synthesized in the real world by the given point in time and/or other points in time. In some implementations, the set of the previously synthesized materials that were synthesized in the real world by or after a given point in time may range between 10,000 to 30,000 previously synthesized materials that were synthesized in the real world by the given point in time and/or other points in time. In some implementations, the set of some of the previously synthesized materials that were synthesized in the real world by or after a given point in time may include at least 20,000 previously synthesized materials that were synthesized in the real world by the given point in time and/or other points in time. The greater the number of previously synthesized materials that were synthesized in the real world by the given point in time and/or other points in time used in training the classifier model, the greater the accuracy the classifier model may be. In some implementations, the set of some of the previously synthesized materials that were synthesized in the real world by or after a given point in time may be increased on the order of tenths, hundredths, thousands, etc.

In some implementations, at least some of the previously synthesized materials of the set of the previously synthesized materials that were synthesized in the real world by or after a given point in time may include at least one shared component and/or relationships. In some implementations, at least some of the previously synthesized materials of the set of the previously synthesized materials that were synthesized in the real world by or after a given point in time may include at least one shared chemical element and/or component.

In some implementations, information component 106 may be configured to generate and/or determine the node information based on the information defining the set of previously synthesized materials. Information component 106 may be configured to represent the individual previously synthesized materials of the set of previously synthesized materials as individual nodes in the network.

In some implementations, information component 106 may be configured to generate and/or determine the node information based on some or all of the previously synthesized materials of the set of previously synthesized materials. Information component 106 may be configured to represent some or all of the previously synthesized materials of the set of the previously synthesized materials as nodes in the network.

Information component 106 may be configured to determine the connections between the individual previously synthesized materials of the set of previously synthesized materials and/or other information. Information component 106 may be configured to determine the connections between the individual previously synthesized materials (e.g., the nodes) in the network and/or other information. Information component 106 may be configured to determine the connections between the individual previously synthesized materials based on one or more shared components and/or relationships between the individual previously synthesized materials.

Information component 106 may be configured to determine the shared components between the individual previously synthesized materials of the set of previously synthesized materials and/or other information. The shared components may include one or more of a shared chemical structure, chemical-relevance, and/or other common elements. Information component 106 may be configured to determine whether the individual previously synthesized materials include the one or more of the shared chemical structure, chemical-relevance, and/or other common elements. If the individual previously synthesized materials include one or more of a shared chemical structure, chemical-relevance, and/or other common elements, information component 106 may determine that there may be connections between the individual previously synthesized materials.

Information component 106 may be configured to determine the relationships between the individual previously synthesized materials of the set of previously synthesized materials and/or other information. The relationships between the individual previously synthesized materials may include one or more of a shared inventor, shared time of discovery, shared location of discovery, shared chemical effect, shared method of discovery, shared time of discovery, and/or other relationships. In some implementations, the relationship between the individual previously synthesized materials may include thermodynamic co-existence information, obtained from material phase diagrams or from the convex-hull of the energy—composition space, where the materials are the nodes and the tie-lines formed between materials are the edges. Information component 106 may be configured to determine whether the individual previously synthesized materials include the one or more of the shared inventor, shared time of discovery, shared location of discovery, shared chemical effects, shared method of discovery, shared time of discovery, shared tie-line in phase diagrams (co-existence) and/or other relationships. If the individual previously synthesized materials include the one or more of the shared inventor, shared time of discovery, shared location of discovery, shared chemical effects, shared method of discovery, shared time of discovery, shared tie-line in phase diagrams (co-existence) and/or other relationships, information component 106 may determine there may be connections between the individual previously synthesized materials.

In some implementations, information component 106 may be configured to generate and/or determine the edge information based on the determined connections between the individual previously synthesized materials in the network. Information component 106 may represent the connections between the individual previously synthesized materials (e.g., the nodes) in the network as edges in the network. Information component 106 may represent the connections between the nodes representing the individual previously synthesized materials in the network as edges in the network.

The edges in the network may be represented by a dataset and/or other representation. The dataset may include one or more values characterizing the individual edges. The dataset of the edges may be associated with the dataset of the nodes. The dataset of the edges may be represented by a matrix with one or more values. The one or more values of the matrix may characterize the connections between the individual previously synthesized materials. The matrix of the edges may be associated with the matrix of the nodes.

Information component 106 may be configured to determine when the individual previously synthesized materials of the set of previously synthesized materials were first synthesized in the real world and/or other information. Information component 106 may be configured to determine points in time the individual previously synthesized materials of the set of previously synthesized materials were first synthesized in the real world. Information component 106 may be configured to determine the year the individual previously synthesized materials of the set of previously synthesized materials were first synthesized in the real world. Information component 106 may be configured to determine the month of the year the individual previously synthesized materials of the set of previously synthesized materials were first synthesized in the real world. Information component 106 may be configured to determine the day of the month of the year the individual previously synthesized materials of the set of previously synthesized materials were first synthesized in the real world. Information component 106 may be configured to determine the time of the day of the month of the year the individual previously synthesized materials of the set of previously synthesized materials were first synthesized in the real world.

In some implementations, information component 106 may be configured to determine an approximate time the individual previously synthesized materials of the set of previously synthesized materials were first synthesized in the real world. Information component 106 may be configured to determine an approximate decade the individual previously synthesized materials of the set of previously synthesized materials were first synthesized in the real world. Information component 106 may be rounded to the point in time the individual previously synthesized materials of the set of previously synthesized materials were first synthesized in the real world to determine an approximate time the individual previously synthesized materials were first synthesized in the real world. Information component 106 may be rounded to the point in time the individual previously synthesized materials of the set of previously synthesized materials were first synthesized in the real world to determine an approximate decade the individual previously synthesized materials were first synthesized in the real world. Information component 106 may round the point in time the individual previously synthesized materials of the set of previously synthesized materials were first synthesized in the real world to the nearest month of a year, the nearest year, the nearest decade, and/or other times.

Information component 106 may be configured to obtain information defining the point in time the individual previously synthesized materials of the set of previously synthesized materials were first synthesized in the real world. Information component 106 may be configured to determine when the individual previously synthesized materials of the set of previously synthesized materials were first synthesized in the real world and/or other information based on publication information and/or other information. The publication information may include information that mentions and/or indicates the synthesis of the individual previously synthesized materials of the set of previously synthesized materials in the real world.

The publication information may specify when the individual previously synthesized materials of the set of previously synthesized materials were first synthesized in the real world from one or more publications, publicly available sources, and/or other databases. The publication information may include one or more of the publications, publicly available sources, and/or other databases. The publicly available sources may include the one or more of the magazine, journal, records, and/or other sources and/or other databases.

In some implementations, information component 106 may be configured to determine the associations between the individual previously synthesized materials and the publication information. In some implementations, information component 106 may be configured to determine the associations between the individual previously synthesized materials of the set of previously synthesized materials and the information that mentions and/or indicates the synthesis of the individual previously synthesized materials in the real world.

Information component 106 may be configured to identify the associations between the individual previously synthesized materials and the publications, publicly available sources, and/or other databases by scanning the information defining the publications, publicly available sources, and/or other databases. Information component 106 may be configured to identify one or more words in the publications, publicly available sources, and/or other databases to determine the associations between the individual previously synthesized materials and the publications, publicly available sources, and/or other databases. For example, information component 106 may be configured to scan a document defining a publication and identify one or more words indicating the associations between the document and the individual previously synthesized materials.

Information component 106 may be configured to determine whether the publications, publicly available sources, and/or other databases mention the synthesis of the individual previously synthesized materials. If the publications, publicly available sources, and/or other databases mention the synthesis of the individual previously synthesized materials, information component 106 may determine an association between the publications, publicly available sources, and/or other databases and the individual previously synthesized materials.

In some implementations, information component 106 may be configured to determine whether the publications, publicly available sources, and/or other databases mentions the synthesis of the individual previously synthesized materials based on metadata of the publications, publicly available sources, and/or other databases. If the metadata indicates the mention of the synthesis of the individual previously synthesized materials, information component 106 may determine an association between the publications, publicly available sources, and/or other databases of the metadata and the individual previously synthesized materials.

Information component 106 may be configured to determine when the individual previously synthesized materials of the set of previously synthesized materials were first synthesized in the real world from the publication dates of the publications, publicly available sources, and/or other databases (e.g., the dates of the publications, publicly available sources, and/or databases was published and/or made available to the public on) associated with the individual previously synthesized materials. Information component 106 may be configured to determine when the individual previously synthesized materials were first synthesized in the real world from the approximate points in time the publications were published and/or first made available to the public.

In some implementations, information component 106 may be configured to identify the publication dates and/or other information of the publications, publicly available sources, and/or other databases. Information component 106 may be configured identify the publication dates and/or other information of the publications, publicly available sources, and/or other databases to determine when the publications, publicly available sources, and/or other databases were published and/or made available to the public.

In some implementations, information component 106 may be configured identify the publication dates and/or other information of the publications, publicly available sources, and/or other databases by scanning the information defining the publications publicly available sources, and/or other databases. Information component 106 may be configured to identify one or more words in the publications publicly available sources, and/or other databases to determine the publication dates. For example, information component 106 may be configured to scan a document defining a publication and identify one or more words indicating when the document was published to determine the publication date of the publication.

In some implementations, information component 106 may be configured to identify the publication dates and/or other information of the publications, publicly available sources, and/or other databases based on the metadata of the publications, publicly available sources, and/or other databases. For example, the metadata of the publications, publicly available sources, and/or other databases may indicate the publication dates.

In some implementations, information component 106 may be configured to determine whether the publications, publicly available sources, and/or other databases mention the synthesis of the individual previously synthesized materials by scanning the information defining the publications, publicly available sources, and/or other databases. Information component 106 may be configured to identify one or more words in the publications, publicly available sources, and/or other databases to determine if the publications, publicly available sources, and/or other databases mention the synthesis of the individual previously synthesized materials. For example, information component 106 may be configured to scan a document defining a publication and identify one or more words that mention the synthesis of the individual previously synthesized materials.

In some implementations, information component 106 may be configured to determine the publications, publicly available sources, and/or other databases mentions of the synthesis of the individual previously synthesized materials based on metadata of the publications, publicly available sources, and/or other databases. If the metadata indicates the mention of the synthesis of the individual previously synthesized materials, information component 106 may determine an association between the publications, publicly available sources, and/or other databases of the metadata and the individual previously synthesized materials.

In some implementations, information component 106 may be configured to generate and/or determine the discovery information based on the determined points in time the individual previously synthesized materials of the set of previously synthesized materials were first synthesized in the real world from the publication information.

The discovery information may be represented by a dataset and/or other representation. The dataset may include one or more values indicating the points in time the individual previously synthesized materials were first synthesized in the real world. The dataset of the discovery information may be associated with the dataset of the nodes. The dataset of the discovery information may be represented by a matrix with one or more values. The one or more values of the matrix may specify the points in time the individual previously synthesized materials were first synthesized in the real world. The matrix of the edges may be associated with the matrix of the nodes.

In some implementations, information component 106 may be configured to generate and/or determine the material network information based on the generated and/or determined node information, edge information, discovery information, and/or other information. Information component 106 may generate the network for the set of previously synthesized materials based on the generated and/or determined material network information.

Information component 106 may represent the individual previously synthesized materials of the set of previously synthesized materials as nodes in the network. The nodes in the network may be specified by the generated and/or determined node information. Information component 106 may represent the connections between the individual previously synthesized materials of the set of previously synthesized materials as edges in the network. The edges in the network may be specified by the generated and/or determined edge information. The generated and/or determined discovery information may specify when the individual previously synthesized materials of the set of previously synthesized materials were first synthesized in the real world.

In some implementations, the network may be used to train a classifier model. The network may include some of the nodes representing the previously synthesized materials of the set of previously synthesized materials. The network with some of the nodes representing the previously synthesized materials may be used to train the classifier model. For example, the network parameter information may be determined for the network with some of the nodes representing the previously synthesized materials. The network parameter information may be used to train the classifier model. The remaining previously synthesized materials of the set of previously synthesized materials may be used to test the classifier model.

Determination component 108 may be configured to determine the network parameter information and/or other information. The network parameter information may specify sets of parameter values for the individual nodes in the network and/or individual previously synthesized materials at discrete points in time over a period of time. The sets of parameter values for an individual node and/or individual previously synthesized materials at the discrete points in time over a period of time may include parameter values at the individual discrete points in time. The individual parameter values may include one or more of a degree parameter, degree centrality parameter, eigenvector centrality parameter, betweenness centrality parameter, clustering coefficient parameter, mean shortest-path parameter, mean degree of neighbors parameter, and/or other parameters.

For example, the centrality parameters, including the degree centrality parameter and eigenvector centrality parameter, may reflect relative importance of a node in influencing synthesis (or material stabilities), emphasizing the number of connections and importance of neighbors, respectively. The centrality parameters may be normalized such that they are mostly independent of the size of the network. The mean shortest-path parameter may be the mean of the number of edges to travel from a node to all other nodes. The clustering coefficient parameter may indicate how closely inter-connected a node and its neighboring nodes are; in other words, how much they cluster together in the network.

In some implementations, the individual parameter values may represent the relationships between the individual node and the other nodes in the network at the individual discrete points in time. In some implementations, the individual parameter values may represent the relationships between the individual node and the network at the individual discrete points in time. The relationships between the individual node and the other nodes in the network or the network at the individual discrete points in time may be a geometric relationship, a mathematical relationship, and/or other relationships at the individual discrete points in time.

The period of time may be from a past point in time to a present point in time. In some implementations, the period of time may be from a first point in time to a second point in time. The points in time may specify a year or the month of a year. The discrete points in time may be points in time between the past point in time and the present point in time. The discrete points in time may include a first discrete point in time, a second discrete point in time, a third discrete point in time, and/or other discrete points in time.

The network parameter information may specify sets of parameter values for the individual nodes in the network and/or individual previously synthesized materials at the first discrete point in time, the second discrete point in time, the third discrete point in time, and/or other discrete points in time. The network parameter information may specify the sets of parameter values for an individual node and/or individual previously synthesized material at the first discrete point in time, the second discrete point in time, the third discrete point in time, and/or other discrete points in time. The network parameter information may specify the individual parameter values of the sets of parameter values of the individual node and/or individual previously synthesized material at the first discrete point in time, the second discrete point in time, the third discrete point in time, and/or other discrete points in time.

For example, a first node and/or a first previously synthesized material may include sets of parameter values at the discrete points in time. A first set of parameter values for the first node and/or the first previously synthesized material may be for the first discrete point in time. The first set of parameter values may include a first parameter value at the first discrete point in time, a second parameter value at the first discrete point in time, a third parameter value at the first discrete point in time, and/or other parameter values at the first discrete point in time. A second set of parameter values for the first node and/or the first previously synthesized material may be for the second discrete point in time. The second set of parameter values may include a fourth parameter value at the second discrete point in time, a fifth parameter value at the second discrete point in time, a sixth parameter value at the second discrete point in time, and/or other parameter values at the second discrete point in time. A third set of parameter values for the first node and/or the first previously synthesized material may be for the third discrete point in time. The third set of parameter values may include a seventh parameter value at the third discrete point in time, an eighth parameter value at the third discrete point in time, a ninth parameter value at the third discrete point in time, and/or other parameter values at the third discrete point in time. Other sets of parameter values for the first node and/or the first previously synthesized material may be for other discrete points in time. The other sets of parameters may include parameter values at the discrete points in time for the first node.

In some implementations, determination component 108 may be configured to obtain the material network information and/or other information. Determination component 108 may be configured to obtain the material network information from electronic storage 122, external resources 120, and/or other storage locations. In some implementations, determination component 108 may be configured to obtain the material network information determined by information component 106.

Determination component 108 may be configured to determine the sets of parameter values for the individual nodes in the network and/or individual previously synthesized materials at the individual discrete points in time based on the material network information. The material network information may define the network for determination component 108 configured to determine the sets of parameter values for the individual nodes in the network and/or individual previously synthesized materials. Determination component 108 may determine the network to determine the sets of parameter values for the individual nodes in the network and/or individual previously synthesized materials from the material network information.

The determination of the sets of parameter values for the individual nodes in the network and/or individual previously synthesized materials at the individual discrete points in time may be based on a network that may change (or evolve) over the discrete points in time of the period of time. The determination of the sets of parameter values for the individual nodes in the network and/or individual previously synthesized materials at the individual discrete points in time may be based on a network at given discrete points in time of the period of time that includes only nodes representing individual previously synthesized materials that were synthesized in the real world by the given discrete points in time. The determination of the sets of parameter values for the individual nodes in the network and/or individual previously synthesized materials at an earlier discrete point in time may include fewer nodes compared to the network at a later discrete point in time.

The network may change (or evolve) over the discrete points in time of the period of time. The network at given discrete points in time of the period of time may include only nodes representing individual previously synthesized materials that were synthesized in the real world by the given discrete points in time. The network at an earlier discrete point in time may include fewer nodes compared to the network at a later discrete point. Determination component 108 may determine the nodes representing individual previously synthesized materials that were synthesized in the real world by the given discrete points in time in the network. Determination component 108 may determine the network at the individual discrete points based on the material network information.

For example, the period of time may be between the year 1990 (e.g., the first discrete point in time) and year 2010 (e.g., the third discrete point in time). The discrete points in time of the period of time may include the year 1990, the year 2000 (e.g., the second discrete point in time), and the year 2010. At the discrete points in time of the year 1990, the network may only include nodes representing individual previously synthesized materials that were synthesized by the year 1990. At the discrete points in time of the year 2000, the network may only include nodes representing individual previously synthesized materials that were synthesized by the year 2000. At the discrete points in time of the year 2010, the network may only include nodes representing individual previously synthesized materials that were synthesized by the year 2010. The network at the discrete points in time of the year 1990 may include fewer nodes compared to the network at the discrete points in time of the year 2010. The network at discrete points in time of the year 2010 may have more nodes compared to the network at discrete points in time of the year 1990 since more previously synthesized materials would have been synthesized by the year 2010 compared to the year 1990.

Determination component 108 may determine the network parameter information based on the material network information. Determination component 108 may determine the network parameter information based the network at the individual discrete points in time. Determination component 108 may determine the change (or evolution) of the network at the individual discrete points in time of the period of time. Determination component 108 may determine the nodes in the network at the individual discrete points in time. Determination component 108 may determine the nodes in the network at a given discrete point in time. Determination component 108 may determine the nodes representing individual previously synthesized materials that were synthesized in the real world by the given discrete points in time.

Determination component 108 may determine the sets of parameter values for the individual nodes and/or individual previously synthesized materials based on the network that change (or evolve) over the discrete points in time of the period of time. The parameter values for the individual node and/or individual previously synthesized materials at the individual discrete points in time may be determined based on the nodes in the network at the individual discrete points. Determination component 108 may determine the sets of parameter values for the individual nodes representing the individual previously synthesized materials that were synthesized and/or not synthesized in the real world by the given discrete points in time in the network. The nodes representing the individual previously synthesized materials that were not synthesized in the real world after the given discrete points in time in the network may not be used to determine the sets of parameter values for the individual nodes representing the individual previously synthesized materials that were synthesized and/or un synthesized in the real world by the given discrete points in time.

Determination component 108 may determine the sets of parameter values for the individual nodes in the network and/or individual previously synthesized materials at the discrete points in time of the period of time. Determination component 108 may determine the parameter values of the set of parameter values at the individual discrete points in time. For example, determination component 108 may determine the parameter values of the set of parameter values at the first discrete point in time, the second discrete point in time, the third discrete point in time, and/or other discrete points in time.

In some implementations, determination component 108 may be configured to store the determined network parameter information and/or other information in electronic storage 122, external resources 120, and/or other storage locations. Determination component 108 may be configured to transmit the determined network parameter information and/or other information to electronic storage 122, external resources 120, and/or other storage locations.

The parameter values for the individual node and/or individual previously synthesized materials at the individual discrete points in time may be different at the different discrete points because the number of nodes in the network may be different. For example, the network at the first discrete point in time may have fewer nodes compared to the network at the third discrete point in time.

In some implementations, determination component 108 may be configured to obtain the network parameter information and/or other information. Determination component 108 may be configured to obtain the network parameter information and/or other information from electronic storage 122, external resources 120, and/or other storage locations.

In some implementations, determination component 108 may determine the sets of parameter values for the individual node and/or individual previously synthesized materials at the individual discrete points in time from a network that includes all the nodes representing all of the previously synthesized materials of the set of previously synthesized materials, wherein at given discrete points in time, only nodes representing previously synthesized materials that were synthesized by the given discrete points in time may be used to determine the sets of parameter values for the individual node and/or individual previously synthesized materials at the given discrete points.

In some implementations, determination component 108 may determine the sets of parameter values for the individual node and/or individual previously synthesized materials at the individual discrete points in time from different versions of the network. The different versions of the network may characterize the network at individual discrete points in time. The different versions of the network characterizing the network at individual discrete points in time with nodes representing the previously synthesized materials of the set of previously synthesized materials that were synthesized by a given point in time. The different versions of the network may include only nodes representing the previously synthesized materials of the set of previously synthesized materials that were synthesized by a given point in time.

By way of non-limiting example, determination component 108 may be configured to determine sets of parameter values of the previously synthesized materials. The sets of parameter values of the previously synthesized materials may be determined by representing the previously synthesized materials as individual nodes in the network at discrete points in time over the period of time and determined based on the network. Aforementioned, the network at a given discrete points in time over the period of time may include nodes representing the previously synthesized materials that were synthesized by the given discrete points in time. The sets of parameter values of the previously synthesized materials not synthesized by the given discrete points in time may be determined by representing the previously synthesized materials as individual nodes, and independently including the individual nodes in the network to determine the sets of parameter values of the individual previously synthesized materials not synthesized by the given discrete points in time. The individual nodes representing the previously synthesized materials not synthesized by the given discrete points in time may not be used to determine the sets of parameter values of the other previously synthesized materials. The previously synthesized materials synthesized by the given discrete points in time are already represented as nodes in the network at the given discrete points, and the sets of parameter values of such previously synthesized material are determined based on the nodes in the network.

In some implementations, determination component 108 may be configured to determine a status of discovery information and/or other information. Determination component 108 may be configured to determine the status of discovery information based on the material network information and/or other information. Determination component 108 may be configured to determine the status of discovery information based on the discovery information and/or other information.

The status of discovery information may define values specifying whether individual previously synthesized materials were synthesized in the real world by the discrete points in time of the period of time. The status of discovery information may specify whether individual previously synthesized materials were synthesized in the real world by the individual discrete points in time. The status of discovery information may specify whether individual nodes representing previously synthesized materials were synthesized in the real world by the discrete points in time of the period of time. For example, a first previously synthesized material may be synthesized in the real world at a first point in time (e.g., the year 1999). The status of discovery information may specify that the first previously synthesized material was not synthesized in the real world by the first discrete point (e.g., the year 1990) in time, and was synthesized in the real world at the second discrete point in time (e.g., the year 2000) and third discrete point in time (e.g., the year 2010).

The status of discovery information may be represented by a dataset and/or other representation. The dataset may specify whether the individual previously synthesized materials were synthesized in the real world by the individual discrete points in time. The dataset of the status of discovery information may be represented by a vector and/or a matrix with one or more values. The one or more values of the matrix may specify whether the individual previously synthesized materials were synthesized in the real world by the individual discrete points in time.

The one or more values in the dataset may specify whether the individual previously synthesized materials were synthesized in the real world by the individual discrete points in time using a binary code and/or other representations. For example, the one or more values in the dataset may specify that the individual previously synthesized materials were synthesized in the real world by the individual discrete points in time with a "1", and not synthesized in the real world by the individual discrete points in time with a "0". The status of discovery information may represent whether the first previously synthesized material was synthesized in the real world by [0, 1, 1]. The "0" indicating that the first previously synthesized material was not synthesized in the real world by the first discrete point in time, and the "1"s indicating that the first previously synthesized material was synthesized in the real world by the second discrete point in time and the third discrete point in time.

In some implementations, determination component 108 may be configured to store the determined status of discovery information and/or other information in electronic storage 122, external resources 120, and/or other storage locations. Determination component 108 may be configured to transmit the determined status of discovery information and/or other information to electronic storage 122, external resources 120, and/or other storage locations.

In some implementations, determination component 108 may be configured to obtain the status of discovery information and/or other information. Determination component 108 may be configured to obtain the status of discovery information and/or other information from one or more of electronic storage 122, external resources 120, and/or other storage locations.

In some implementations, determination component 108 may be configured to obtain synthesis information and/or other information. Determination component 108 may be configured to obtain the synthesis information from one or more of electronic storage 122, external resources 120, and/or other storage locations. The synthesis information may specify one or more synthesized materials that were synthesized in the real world but not included in the set of previously synthesized materials. The one or more synthesized materials may be materials that were previously unsynthesized materials. The one or more synthesized materials may be materials that were previously synthesized but not included in the set of previously synthesized materials. In some implementations, the one or more synthesized materials may be synthesized before some or all of the previously synthesized materials of the set of previously synthesized materials, but not included in the set of previously synthesized materials.

The one or more synthesized materials may be one or more hypothetical materials, computer generated hypothetical materials, theoretical materials that were previously unsynthesized in the real world but become synthesized at a point in time, and/or other materials. The one or more synthesized materials may have been newly synthesized materials. In some implementations, the synthesis information may define the one or more synthesized materials and the time of first synthesis of the one or more synthesized materials.

Determination component 108 may be configured to introduce the synthesized materials in the set of previously synthesized materials. Determination component 108 may amend or alter the network with the set of previously synthesized materials by introducing the synthesized materials in the set of previously synthesized materials. Determination component 108 may be configured to introduce the synthesized materials as nodes in the network. Determination component 108 may be configured to determine the connections between the individual synthesized materials and the individual previously synthesized materials. Determination component 108 may represent the connections between the individual synthesized materials and the individual previously synthesized materials as edges in the network.

Determination component 108 may be configured to determine the sets of parameter values for the individual nodes in the network at discrete points in time over a period of time including the nodes representing the synthesized materials and the individual previously synthesized materials. Determination component 108 may be configured to determine the sets of parameter values for individual previously synthesized materials including the synthesized materials. The determination of the sets of parameter values for the individual nodes in the network and/or individual previously synthesized materials including the synthesized materials may include the network at given discrete points in time of the period of time with nodes representing individual previously synthesized materials and/or individual synthesized materials that were synthesized in the real world by the given discrete points in time. The network at given discrete points in time of the period of time may include only nodes representing individual previously synthesized materials and/or individual synthesized materials that were synthesized in the real world by the given discrete points in time. The inclusion of the synthesized materials may alter the sets of parameter values for the individual nodes in the network and/or individual previously synthesized materials since there may be additional nodes in the network that were previously not included. The inclusion of the synthesized materials may change the predicted probability of materials being synthesized in the real world at the discrete points in time.

Training component 110 may be configured to train a classifier model and/or other information. Training component 110 may be configured to determine classifier information and/or other information. The classifier information may define the trained classifier model and/or other information. Training component 110 may be configured to train the classifier model based on the material network information and/or other information. Training component 110 may be configured to train the classifier model based on the network defined by the material network information and/or other information. Training component 110 may be configured to train the classifier model based on the network with only some of the previously synthesized materials of the set of previously synthesized materials. Training component 110 may be configured to test the trained classifier model with the remaining previously synthesized materials of the set of previously synthesized materials. Training component 110 may be configured to test the trained classifier model to determine the accuracy of the classifier model. Training component 110 may be configured to train the classifier model based on the network with 80% of the previously synthesized materials of the set of previously synthesized materials, and test the trained classifier model with the remaining 20% of the previously synthesized materials. In some implementations, training component 110 may be configured to train the classifier model based on the network with at least 50% of the previously synthesized materials of the set of previously synthesized materials, and test the trained classifier model with the remaining percentage of previously synthesized materials. In some implementations, the classifier model may be trained with the previously synthesized materials of the set of previously synthesized materials and/or other materials. For example, the classifier model may be trained with the previously synthesized materials of the set of previously synthesized materials and unsynthesized materials.

In some implementations, training component 110 may be configured to train the classifier model based on the network parameter information, the discovery information, and/or other information. Training component 110 may be configured to train the classifier model based on the network parameter information, the status of discovery information, and/or other information. Training component 110 may be configured to train the classifier model to generate probability information and/or other information.

In some implementations, training component 110 may be configured to train the classifier model based on the network parameter information determined from the set of previously synthesized materials, the status of discovery information, and/or other information. In some implementations, training component 110 may be configured to retrain (or alter) the classifier model based on the network parameter information determined from the set of previously synthesized materials and synthesized materials, the status of discovery information, and/or other information. In some implementations, training component 110 may be configured to train the classifier model based on the network parameter information determined from the set of previously synthesized materials and synthesized materials, the status of discovery information, and/or other information. In some implementations, training component 110 may be configured to train the classifier model using the network parameter information determined from the set of previously synthesized materials and synthesized materials, the status of discovery information, and/or other information.

Training component 110 may train the classifier model using one or more machine learning techniques, classification techniques, training techniques, and/or other techniques. Training component 110 may train the classifier model using one or more supervised and/or unsupervised machine-learning techniques. Training component 110 may train the classifier model using one or more supervised and/or unsupervised machine-learning techniques based on material network information, the network parameter information, the discovery information, the status of discovery information, and/or other information. Training component 110 may train the classifier model using one or more supervised and/or unsupervised machine-learning techniques based on the network parameter information, the status of discovery information, and/or other information. Training component 110 may train the classifier model using one or more supervised and/or unsupervised machine-learning techniques based on the sets of parameter values of the individual nodes in the network at discrete points in time of the period of time, the values specifying whether individual previously synthesized materials were synthesized in the real world by the discrete points in time of the period of time, and/or other information.

Training component 110 may train the classifier model using one or more of a sequential machine-learning method, recurrent sliding window machine-learning method, random forest machine-learning method, neural network machine-learning method, and/or other machine-learning methods. Training component 110 may train the classifier model using a combination of the one or more of the sequential machine-learning method, recurrent sliding window machine-learning method, linear regression machine-learning method, random forest machine-learning method, neural network machine-learning method, principal component analysis, and/or other machine-learning methods.

Training component 110 may be configured to store the classifier information in one or more of electronic storage 122, external resources 120, and/or other storage locations. Training component 110 may be configured to store the trained classifier model in one or more of electronic storage 122, external resources 120, and/or other storage locations.

Training component 110 may train the classifier model to generate probability information and/or other information. Training component 110 may generate probability information from the classifier model. The classifier model may generate probability information that may specify values specifying probabilities for materials being successfully synthesized in the real world at the individual discrete points in time of the period of time. For example, the materials may include the previously synthesized materials, unsynthesized materials, and/or other materials. The classifier model may be trained to generate values specifying probabilities for materials being successfully synthesized in the real world at the first discrete point in time, the second discrete point in time, the third discrete point in time, and/or other discrete points in time. The values specifying probabilities for the materials being successfully synthesized in the real world may indicate a likelihood the materials will be successfully synthesized for the first time in the real world at the individual discrete points in time.

In some implementations, synthesis of a previously unsynthesized material may alter the probabilities of the materials being successfully synthesized in the real world at the individual discrete points in time of the period of time. Training component 110 may be configured to identify the synthesis of a previously unsynthesized material that may alter the probabilities of the materials being successfully synthesized in the real world at the individual discrete points in time of the period of time. Training component 110 may be configured to update or retrain (or alter) the classifier model when the synthesis of a previously unsynthesized material is identified. The synthesis of a previously unsynthesized material may be introduced into the set of previously synthesized material. In some implementations, the identification of the synthesis of a previously unsynthesized material may occur when information defining the synthesis of the previously unsynthesized material is available. The previously unsynthesized material may be introduced in the set of previously synthesized material when the synthesis of the previously unsynthesized material is identified. The sets of parameter values for the network including the set of previously synthesized material and previously unsynthesized material may be determined in the same way described in determination component 108. The classifier model may be updated and/or retrained based on the new sets of parameter values. In some implementations, the synthesis of a previously unsynthesized material may be the defined by the synthesized materials.

In some implementations, training component 110 may be configured to determine a change in the probabilities of the materials being successfully synthesized in the real world at the individual discrete points in time of the period of time when a previously unsynthesized material was synthesized for the first time in the real world. In some implementations, training component 110 may be configured to determine the difference in the probabilities of the materials being successfully synthesized in the real world at the individual discrete points in time of the period of time when the synthesized materials were introduced in the set of previously synthesized materials. Training component 110 may compare the difference in the probabilities of the materials being successfully synthesized in the real world at the individual discrete points in time of the period of time before and after the synthesized materials were introduced in the set of previously synthesized materials to determine the difference in the probabilities. In some implementations, training component 110 may compare the difference in the probabilities generated by the classifier model based on the network parameter information determined from the set of previously synthesized materials, the status of discovery information, and/or other information and the probabilities generated by the classifier model based on the network parameter information determined from the set of previously synthesized materials and synthesized materials, the status of discovery information, and/or other information. Training component 110 may be configured to generate one or more values specifying the difference in the probabilities.

Prediction component 112 may be configured to generate values specifying probabilities for the materials being successfully synthesized in the real world at the individual discrete points in time for materials. Prediction component 112 may be configured to generate the values specifying the probability information and/or other information. Prediction component 112 may be configured to generate values specifying probabilities for the one or more of the hypothetical materials, computer generated hypothetical materials, theoretical materials, the previously synthesized materials, and/or other materials being successfully synthesized in the real world at the individual discrete points in time for materials. In some implementations, prediction component 112 may be configured to generate values specifying probabilities for the one or more of the hypothetical materials, computer generated hypothetical materials, theoretical materials, and/or other materials being successfully synthesized in the real world at the individual discrete points in time for materials. Prediction component 112 may be configured to generate the values specifying the probability information and/or other information based on the classifier model and/or other information.

For example, the values specifying probabilities for a material being successfully synthesized in the real world may include a first value specifying a probability the material will be successfully synthesized in the real world at the first discrete point in time, a second value specifying a probability the material will be successfully synthesized in the real world at the second discrete point in time, a third value specifying a probability the material will be successfully synthesized in the real world at the third discrete point in time, and/or other values specifying other probabilities the material will be successfully synthesized in the real world at other discrete points in time. In some implementations, the material may be an unsynthesized material and/or other material.

Prediction component 112 may be configured to obtain the trained classifier model from training component 110 and/or other locations. Prediction component 112 may be configured to obtain the trained classifier model from one or more of electronic storage 122, external resource 120, and/or other locations. Prediction component 112 may be configured to generate the probability information using the trained classifier model and/or other information.

Prediction component 112 may be configured to obtain material information defining the materials (including the hypothetical materials, computer generated hypothetical materials, theoretical materials, unsynthesized materials, the previously synthesized materials, and/or other materials). The materials may include a first material, a second material, a third material, and/or other materials. In some implementations, the material information may include unsynthesized material information defining unsynthesized materials. The unsynthesized materials may include unsynthesized hypothetical materials, computer generated hypothetical materials, theoretical materials, and/or other unsynthesized materials.

Prediction component 112 may be configured to generate values specifying probabilities for the materials being successfully synthesized in the real world at the individual discrete points in time based on the classifier model and the material information. In some implementations, the material information may define sets of parameter values for the materials. Prediction component 112 may apply the classifier model to the sets of parameter values for the materials to generate values specifying probabilities for the materials being successfully synthesized in the real world at the individual discrete points in time for materials.

Prediction component 112 may be configured to determine the sets of parameter values for the materials and/or other information. Prediction component 112 may be configured to determine the sets of parameter values for the materials by introducing the materials in the network, and determining the sets of parameter values for the materials in the same way sets of parameter values were determined in determination component 108.

By way of non-limiting example, prediction component 112 may represent the materials as individual nodes, and independently include the individual nodes in the network to determine the sets of parameter values of the materials. The individual nodes representing the materials at the given discrete points in time may not be used to determine the sets of parameter values of the other materials.

For example, prediction component 112 may be configured to determine an association between a first material and the individual previously synthesized materials represented as nodes in the network. The first material may be an unsynthesized materials and/or other materials. Prediction component 112 may be configured to determine the connections between the individual previously synthesized materials of the set of previously synthesized materials and the first material. Prediction component 112 may be configured to determine the connections between the individual previously synthesized materials of the set of previously synthesized materials and the first material based on one or more shared components and/or relationships between the individual previously synthesized materials of the set of previously synthesized materials and the first material.

Prediction component 112 may introduce the first material in the network as a node in the network. Prediction component 112 may determine the edges of the node representing the first material based on the connections between the individual previously synthesized materials of the set of previously synthesized materials and the first material. Prediction component 112 may introduce the first material in the network as a node at the discrete point in time, at which the probability of synthesis of that material is of interest. There may be more than one discrete points in time that the probabilities can be of interest to a user, and for each such discrete point in time, the first material may be introduced to the corresponding network of that time.

Prediction component 112 may be configured to determine the sets of parameter values for the node representing the first material in the network at the individual discrete points in time. Prediction component 112 may be configured to determine the sets of parameter values for the node representing the first material in the network at the individual discrete points in time in the same way the sets of parameter values were determined by the determination component 108.

In some implementations, prediction component 112 may be configured to obtain the sets of parameter values for the node representing the first material in the network at the individual discrete points in time. Prediction component 112 may be configured to obtain the sets of parameter values for the node representing the first material in the network at the individual discrete points in time from one or more of electronic storage 122, external resource 120, and/or other storage locations.

Prediction component 112 may be configured to apply the classifier model to the sets of parameter values for the node representing the first material to generate the probability information and/or other information. Prediction component 112 may be configured to apply the classifier model to the sets of parameter values for the node representing the first material to generate the values specifying probabilities for materials being successfully synthesized in the real world at the individual discrete points in time of the period of time.

In some implementations, the probabilities for materials being successfully synthesized in the real world may increase over time. For example, the probabilities for materials being successfully synthesized in the real world at the second discrete point in time may be greater than the probabilities for materials being successfully synthesized in the real world at the first discrete point in time.

In some implementations, prediction component 112 may be configured to determine a change in the determined values specifying the probabilities of the materials being successfully synthesized in the real world at the individual discrete points in time of the period of time when a previously unsynthesized material was synthesized for the first time in the real world. Prediction component 112 may be configured to obtain an updated or retrain classifier model. Prediction component 112 may be configured to determine the values specifying the probabilities of the materials being successfully synthesized in the real world at the individual discrete points in time of the period of time based on the updated or retrain classifier model. Prediction component 112 may be configured to compare the values specifying the probabilities generated by the classifier model and the updated or retrain classifier model to determine a change in the values specifying the probabilities of the materials being successfully synthesized in the real world at the individual discrete points in time of the period of time. In some implementations, the change in the values specifying the probabilities of the materials being successfully synthesized in the real world at the individual discrete points in time of the period of time may affect some materials more than others. For example, if the updated or retrained classifier model was determined based on the synthesis of a previously unsynthesized material that is closely associated with a material, the change in the values specifying the probabilities for the material may be greater.

Presentation component 114 may be configured to effectuate presentation of an interface and/or other information. Presentation component 114 may be configured to effectuate presentation of the interface on computing platform(s) 140 and/or other devices. Presentation component 114 may be configured to effectuate presentation of the interface on a display of computing platform(s) 140 and/or other devices. The interface may be a graphical user interface and/or other interfaces.

The interface may include a virtual space, one or more virtual objects, and/or other information. The one or more virtual objects may be positioned through a topography of the virtual space. The topography of the virtual space may be a two-dimensional virtual space, a three-dimensional virtual space, and/or other virtual spaces. The one or more virtual objects may include one or more text boxes, text input fields, buttons, menus, graphs, tables, widgets, graphical representation of information, and/or other virtual objects. More than one virtual objects may be positioned through the topography of the virtual space at the same time. The virtual objects may be configured to facilitate presentation of information, obtain user instructions, and/or perform other functions. The virtual objects may be configured to facilitate visualization of information and/or perform other functions.

Presentation component 114 may be configured to effectuate presentation of the probability information and/or other information. Presentation component 114 may be configured to effectuate presentation of the probability information on computing platform(s) 140 and/or other devices. Presentation component 114 may be configured to effectuate presentation of the probability information on the interface. Presentation component 114 may be configured to effectuate presentation of the probability information on the one or more virtual objects positioned within the topography of the virtual space.

For example, presentation component 114 may be configured to effectuate presentation of the probability information on one or more a table, a graph, a graphical representation, and/or other presentation methods on the interface. The one or more table, graph, graphical representation may be represented by the virtual objects. Presentation component 114 may be configured to effectuate presentation of the probability information on the interface such that a user may access and/or review the probability information.

The presentation of the probability information by presentation component 114 may include the presentation of the values specifying probabilities for the materials being successfully synthesized in the real world at the individual discrete points in time of the period of time. The values specifying probabilities for the materials being successfully synthesized in the real world at the individual discrete points in time of the period of time may be presented by the one or more virtual objects positioned within the topography of the virtual space.

For example, the values specifying probabilities for the materials being successfully synthesized in the real world at the individual discrete points in time of the period of time may be presented in a table, a graph, a graphical representation of the values, and/or other presentation methods. The one or more table, graph, graphical representation may be represented by the virtual objects.

In some implementations, presentation component 114 may be configured to effectuate presentation of the values specifying probabilities for the materials being successfully synthesized in the real world at some of the discrete points in time of the period of time. In some implementations, the values specifying probabilities for the materials being successfully synthesized in the real world at some of the discrete points in time of the period of time may be presented on a first virtual object, and the values specifying probabilities for the materials being successfully synthesized in the real world at some of the discrete points in time of the period of time may be presented on a second virtual object.

In some implementations, presentation component 114 may be configured to effectuate presentation of the values specifying probabilities for some of the materials being successfully synthesized in the real world at some of the discrete points in time of the period of time. In some implementations, the values specifying probabilities for some of the materials being successfully synthesized in the real world at some of the discrete points in time of the period of time may be presented on the first virtual object, and the values specifying probabilities for some of the materials being successfully synthesized in the real world at some of the discrete points in time of the period of time may be presented on the second virtual object.

In some implementations, presentation component 114 may be configured to effectuate presentation of the change in the determined values specifying the probabilities of the materials being successfully synthesized in the real world at the individual discrete points in time of the period of time when a previously unsynthesized material was synthesized for the first time in the real world. In some implementations, presentation component 114 may be configured to effectuate presentation of the change in the determined values specifying the probabilities of the materials being successfully synthesized in the real world at the individual discrete points in time of the period of time when a change in the determined values specifying the probabilities for a material exceeds a predetermined threshold.

In some implementations, presentation component 114 may be configured to effectuate presentation of one or more notifications and/or other information. The one or more notifications may inform a user of the synthesis of the previously unsynthesized material, a change in the determined values specifying the probabilities for a material exceeding a predetermined threshold, an increase and/or decrease in probabilities for a material being successfully synthesized in the real world at the discrete points in time, and/or other information. The one or more notifications may be presented via the one or more virtual objects.

In some implementations, presentation component 114 may be configured to effectuate presentation of a progress report for unsynthesized materials and/or other information. The progress report for the unsynthesized materials may specify the probabilities of the individual unsynthesized materials being synthesized in the real world at the individual discrete points in time of the period of time, ranks of the individual unsynthesized materials based on the probabilities of the individual unsynthesized materials being synthesized in the real world at the individual discrete points in time of the period of time, a unsynthesized material that will most likely be synthesized in the real world at the individual discrete points in time of the period of time, a unsynthesized material that will most likely be synthesized in the real world at a present point in time, and/or other information.

In some implementations, the progress report for unsynthesized materials may indicate how the probabilities of an unsynthesized material being synthesized in the real world will change as a result of another unsynthesized material being synthesized in the real world. In some implementations, the progress report for unsynthesized materials highlight or indicate an unsynthesized material a user should focus their investment on. The investment may be time or resource investments.

In some implementations, the user may decide the information presented by the one or more virtual objects on the topography of the virtual space. The user may decide the information presented by providing computing platform(s)

140 with the user instructions. In some implementations, the user may instruct prediction component 112 to generate values specifying probabilities for materials chosen by the user. For example, the user may instruct prediction component 112 to generate values specifying probabilities for the materials (chosen by the user) being successfully synthesized in the real world at the individual discrete points in time of the period of time.

In some implementations, the user may instruct prediction component 112 to introduce a previously unsynthesized material in the training or alteration of the classifier model. The user may view the changes in the values specifying probabilities for the materials being successfully synthesized in the real world at the individual discrete points in time of the period of time as a result of the previously unsynthesized material being introduced in the training or alteration of the classifier model.

In some implementations, presentation component 114 may be configured to obtain user inputs defining the user instructions from one or more users. Presentation component 114 may be configured to obtain user inputs from computing platform(s) 140. Presentation component 114 may be configured to obtain user inputs from the user's interaction with the interface and/or other components. Presentation component 114 may be configured to obtain user inputs from user interaction with the one or more virtual objects positioned within the topography of the virtual space. User interaction with the one or more virtual objects may be a user selection of the one or more virtual objects.

The user input may include one or more of a body gesture input, touch gesture input, controller input, text input, audio input, movement input, and/or other inputs. The user input may specify one or more selections of the virtual objects within the topography of the virtual space.

The touch gesture input may include information defining one or more movements. The movements may include one or more of a finger press, a finger tap, a finger swipe, a finger flick, a finger drag, a pinch, a touch-and-hold, a scroll, and/or other finger movements. These movements may similarly be carried out using a tool, such as a stylus.

The controller input may include information defining one or more of a key/button pressing input, a key/button tapping input, a swiping input, a flick input, a drag input, a key/button press-and-hold input, a scroll input, and/or other inputs from a controller. The controller input may include one or more of a movement of a mouse, a movement of a mouse while holding a button on the mouse, a press of one or more keys of a keyboard, a movement of a joystick, a movement of a joystick while holding of a button on a controller, and/or other controller inputs.

In some implementations, the text input may be obtained from a keyboard, a voice recognition device, and/or other devices. The text input may include one or more words in one or more languages. The one or more words may form one or more sentences in one or more languages.

The audio input may include information defining audio signals of a user. The audio signal of the user may be captured by a microphone and/or other audio capture devices. The audio signals from the user may be a voice command. In some implementations, instructions may be associated with the voice commands.

The movement input may include information defining movements of computing platform(s) 140 and/or other devices. The movements may include a shaking movement, a projection movement, a rotation movement, and/or other movements. The shaking movement may include a user shaking computing platform(s) 140 and/or other devices.

In some implementations, server(s) 102, computing platform(s) 140, and/or external resource(s) 120 may be operatively linked via one or more electronic communication links. For example, such electronic communication links may be established, at least in part, via a network 103 such as the Internet and/or other networks. It will be appreciated that this is not intended to be limiting, and that the scope of this disclosure may include implementations in which server(s) 102, computing platform(s) 140, and/or external resource(s) 120 may be operatively linked via some other communication media.

In some implementations, external resource(s) 120 may include sources of information, hosts and/or providers of virtual environments outside of system 100, external entities participating with system 100, and/or other resources. In some implementations, some or all of the functionality attributed herein to external resource(s) 120 may be provided by resources included in system 100.

In some implementations, Server(s) 102 may include electronic storage(s) 122, processor(s) 124, and/or other components. Server(s) 102 may include communication lines or ports to enable the exchange of information with a network and/or other computing devices. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing devices operating together as server(s) 102.

In some implementations, electronic storage(s) 122 may include electronic storage media that electronically stores information. The electronic storage media of electronic storage(s) 122 may include one or both of system storage that is provided integrally (i.e., substantially nonremovable) with server(s) 102 and/or removable storage that is removably connectable to server(s) 102 via, for example, a port (e.g., a USB port, a firewire port, etc.) or a drive (e.g., a disk drive, etc.). Electronic storage(s) 122 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage(s) 122 may include one or more virtual storage resources (e.g., cloud storage, a virtual private network, and/or other virtual storage resources). Electronic storage(s) 122 may store software algorithms, information determined by processor(s) 124, information received from server(s) 102, information received from computing platform(s) 140, and/or other information that enables server(s) 102 to function as described herein.

In some implementations, processor(s) 124 may be configured to provide information processing capabilities in server(s) 102. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same computing platform, or processor(s) 124 may represent processing functionality of a plurality of devices operating in coordination. The processor(s) 124 may be configured to execute computer-readable instruction components 106, 108, 110, 112, 114, and/or other components. The processor(s) 124 may be configured to execute components 106, 108, 110,112, 114, and/or other components by software; hardware; firmware; some combination of software, hardware, and/or firmware; and/or other mechanisms for configuring processing capabilities on processor(s) 124.

It should be appreciated that although components 106, 108, 110, 112, and 114 are illustrated in FIG. 1 as being co-located within a single processing unit, in implementations in which processor(s) 124 may include multiple processing units, one or more of components 106, 108, 110, 112, and/or 114 may be located remotely from the other components. The description of the functionality provided by the different components 106, 108, 110, 112, and/or 114 described herein is for illustrative purposes, and is not intended to be limiting, as any of components 106, 108, 110, 112, and/or 114 may provide more or less functionality than is described. For example, one or more of components 106, 108, 110, 112, and/or 114 may be eliminated, and some or all of its functionality may be provided by other ones of components 106, 108, 110, 112, and/or 114. As another example, processor(s) 124 may be configured to execute one or more additional components that may perform some or all of the functionality attributed herein to one of components 106, 108, 110, 112, and/or 114.

FIG. 4 illustrates an example of the information defined by the material network information. The information defined by the material network information may include a list of previously synthesized materials 400 and the discovery time 500 of the individual previously synthesized materials of list of previously synthesized materials 400. List of previously synthesized materials 400 may include a material 401, a material 402, a material 403, a material 404, a material 405, a material 406, a material 407, a material 408, a material 409, a material 410, and other materials. Discovery time 500 may indicate the point in time the individual materials of the list of previously synthesized materials 400 were first synthesized in the real world. Material 401 may be first synthesized in the real world at a time 501, material 402 may be first synthesized in the real world at a time 502, material 403 may be first synthesized in the real world at a time 503, material 404 may be first synthesized in the real world at a time 504, material 405 may be first synthesized in the real world at a time 505, material 406 may be first synthesized in the real world at a time 506, material 407 may be first synthesized in the real world at a time 507, material 408 may be first synthesized in the real world at a time 508, material 409 may be first synthesized in the real world at a time 509, material 410 may be first synthesized in the real world at a time 510, and all the other materials may be first synthesized in the real world at other times. In some implementations, some of the previously synthesized materials in list of previously synthesized materials 400 may be first synthesized in the real world at the same time. List of previously synthesized materials 400, discovery time 500, and/or other information may be used to train the classifier model.

Figure 5:
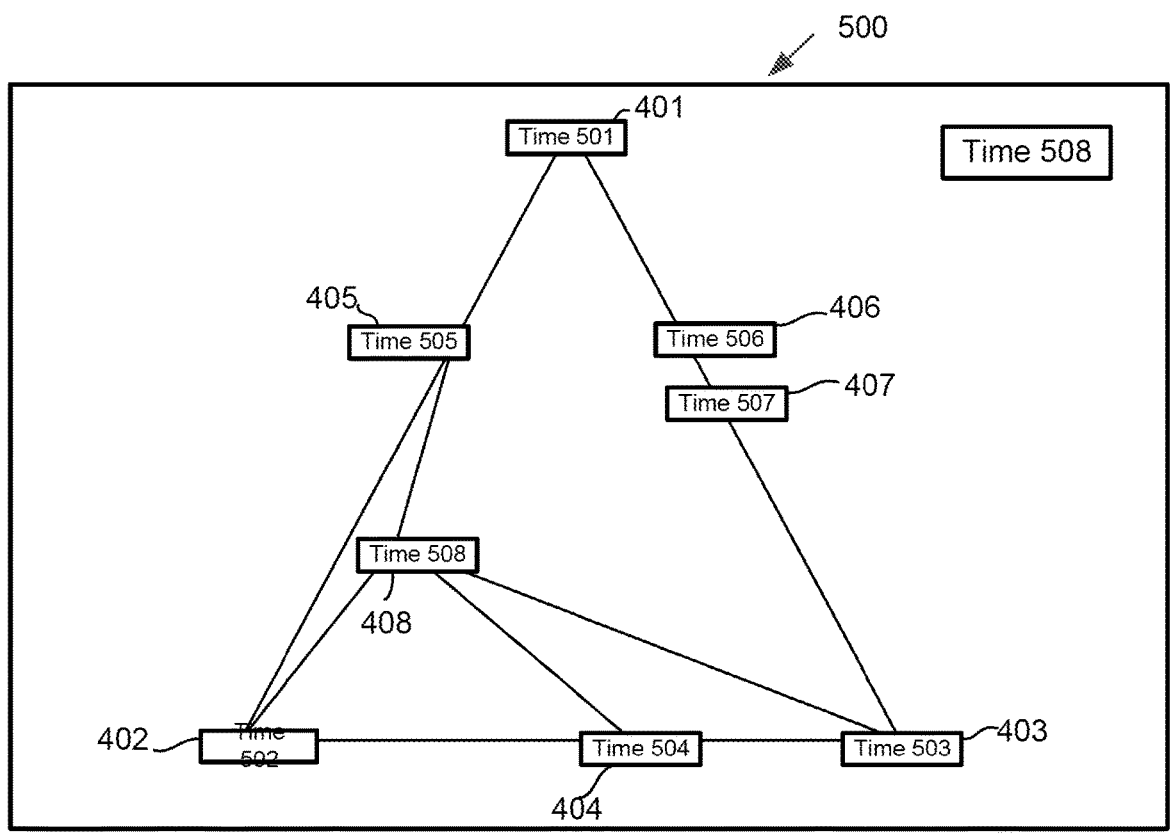
FIG. 5 illustrates an example of a network at a given discrete point in time, in accordance with one or more implementations.
Figure 6:
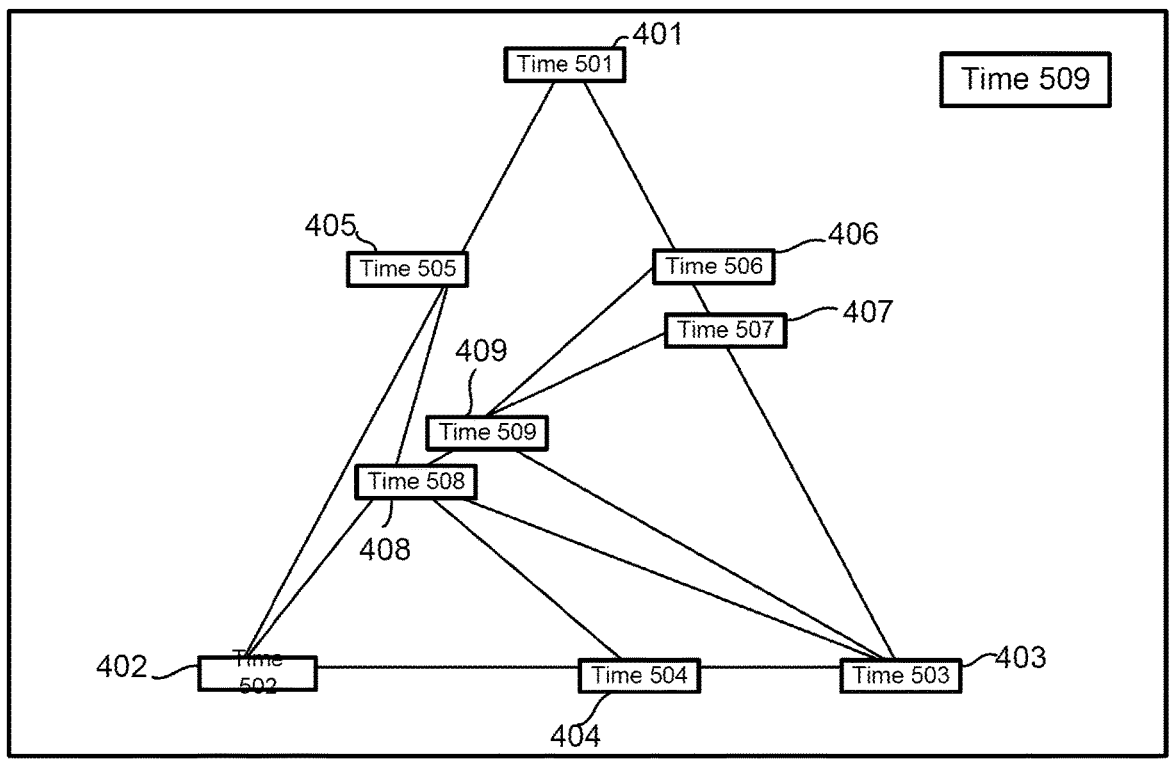
FIG. 6 illustrates an example of the network at another given discrete point in time, in accordance with one or more implementations.
Figure 7:
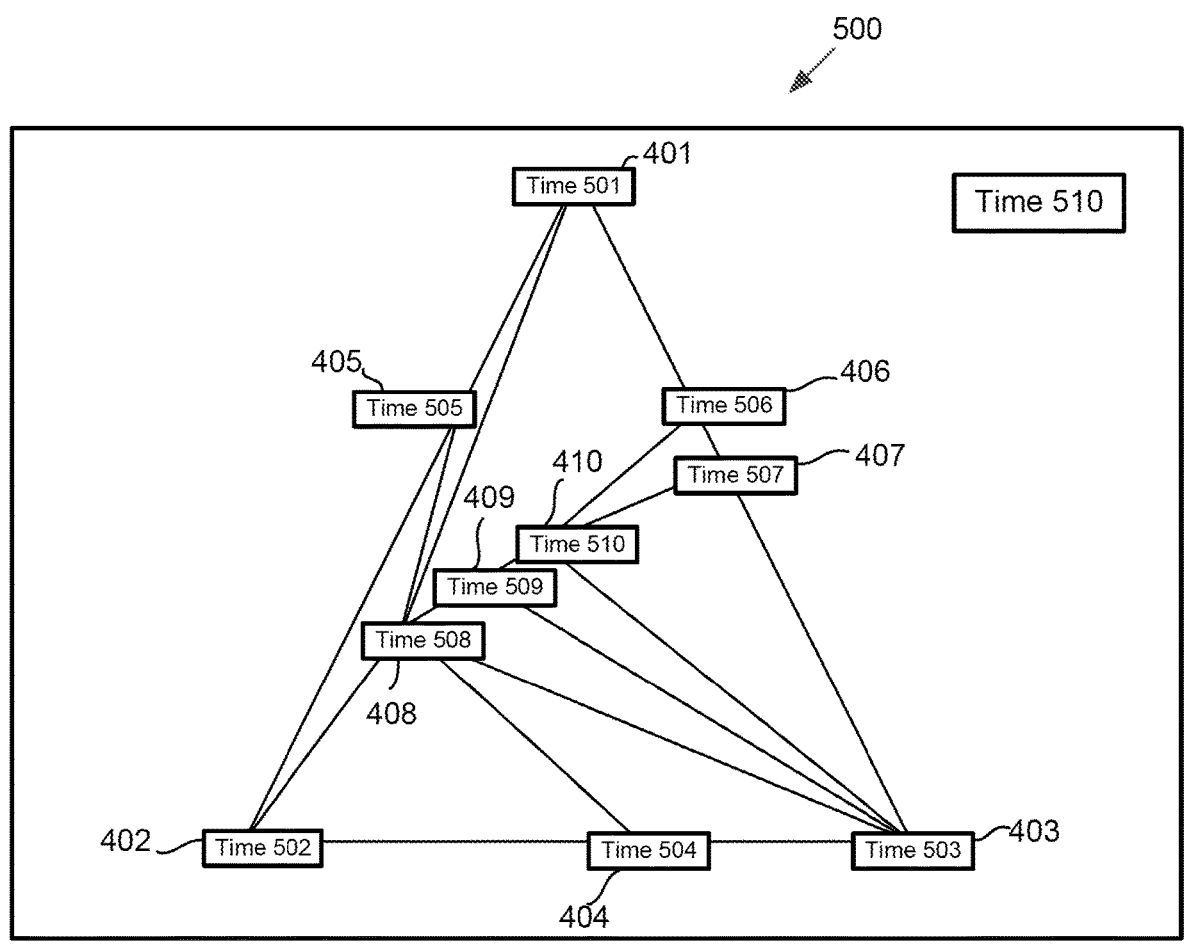
FIG. 7 illustrates an example of the network at another given discrete point in time, in accordance with one or more implementations.

FIGS. 5 to 7 illustrates an example of a network 500 defined by the material network information at individual discrete points in time over a period of time. The period of time may be between time 501 to time 510. The individual discrete points in time may include time 501, time 502, time 503, time 504, time 505, time 506, time 507, time 508, time 509, time 510, and/or other discrete points in time. In some implementations, the individual discrete points in time may include time 501, time 505, time 510, and/or other discrete points in time. In some implementations, the individual discrete points in time may include time 508, time 509, time 510, and/or other discrete points in time. The individual previously synthesized materials of list of previously synthesized materials 400 may be characterized by nodes in the network. The connections between the individual previously synthesized materials may be characterized by edges in the network.

In some implementations, individual nodes of network 500 may be associated with a timestamp and/or other information. The timestamp may specify points in time the nodes representing the individual previously synthesized materials of list of previously synthesized materials 400 were first synthesized in the real world. Network 500 at a given discrete point in time may include the nodes representing the individual previously synthesized materials of list of previously synthesized materials 400 that were synthesized in the real world by the given discrete point in time. For example, network 500 at time 508 may include nodes representing the individual previously synthesized materials of list of previously synthesized materials 400 that were synthesized in the real world by time 508.

In some implementations, one or more nodes representing the individual previously synthesized materials of list of previously synthesized materials 400 may be included (e.g., added) in network 500 at the individual given discrete points in time. For example, at time 509 network 500 is modified (from network 500 at time 508) to include nodes representing the individual previously synthesized materials of list of previously synthesized materials 400 that were synthesized in the real world by time 509. At time 510 network 500 is modified (from network 500 at time 509) to include nodes representing the individual previously synthesized materials of list of previously synthesized materials 400 that were synthesized in the real world by time 510.

Although the illustration only shows one node being added to network 500 at individual time steps of the discrete points in time, network 500 at individual time steps of the discrete points in time is not limited to only one node being added at individual time steps. If more than one nodes representing the individual previously synthesized materials of list of previously synthesized materials 400 that were synthesized in the real world at a given point in time, the nodes may be added to network 500.

FIG. 5 illustrates an example of network 500 at the discrete points in time of time 508. Network 500 may include nodes representing the previously synthesized materials of list of previously synthesized materials 400 that were synthesized by time 508.

FIG. 6 illustrates an example of network 500 at the discrete points in time of time 509. Network 500 may include nodes representing the previously synthesized materials of list of previously synthesized materials 400 that were synthesized by time 509.

FIG. 7 illustrates an example of network 500 at the discrete points in time of time 510. Network 500 may include nodes representing the previously synthesized materials of list of previously synthesized materials 400 that were synthesized by time 510.

Sets of parameter values for the individual nodes in network 500 at the discrete points in time of the period of time period of time may be determined. The sets of parameter values for the individual nodes in network 500 and/or other information may be used to train a classifier model. For example, sets of parameter values for the node representing material 401 of network 500 may be determined at time 508, time 509, and time 510.

Figure 8:
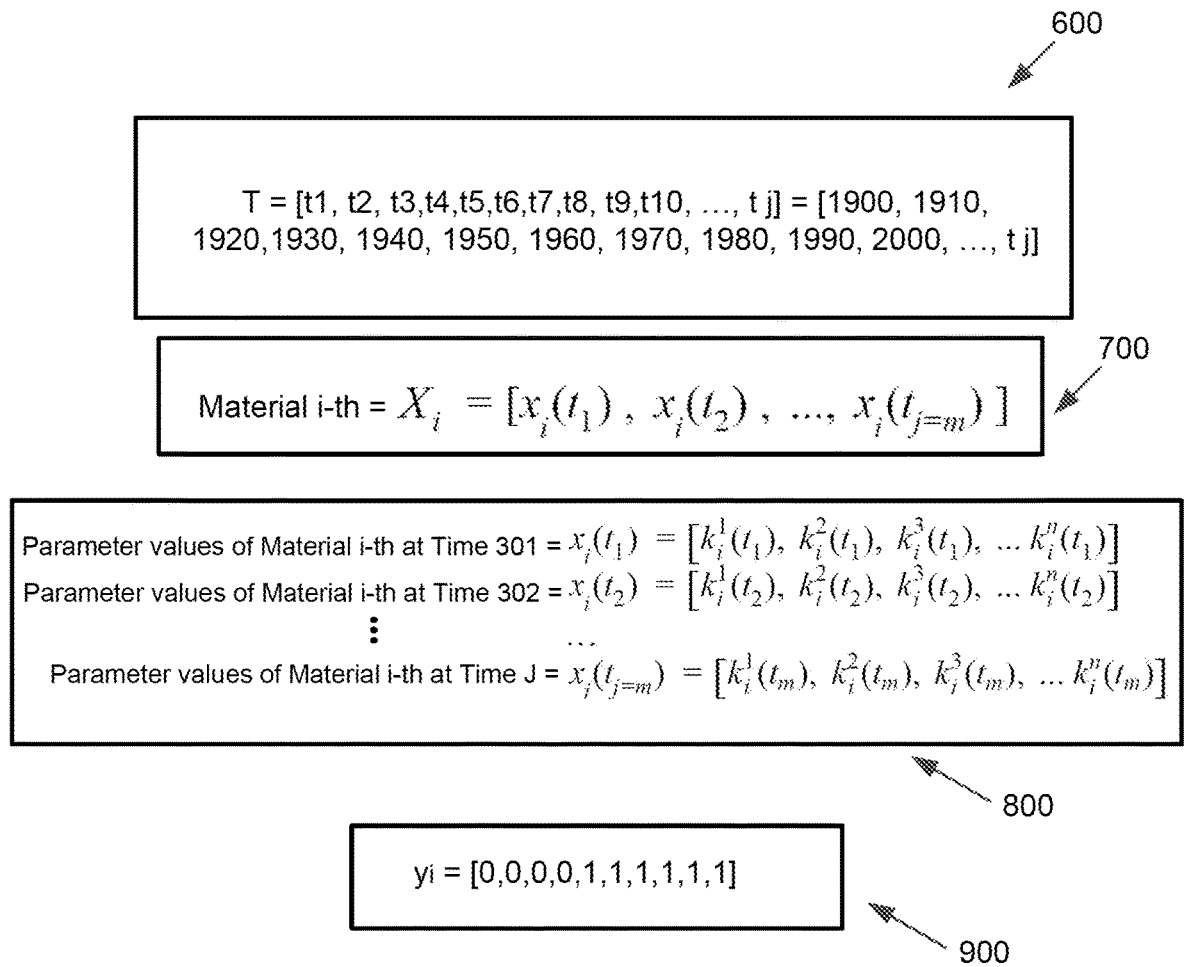
FIG. 8 illustrates an example of sets of parameter values of an individual node in the network at discrete points in time of a period of time, in accordance with one or more implementations.

FIG. 8 illustrates an example of the sets of parameter values of an individual node in network 500 at the discrete points in time (e.g., t1 to t10) of the period of time (e.g., T). The individual node may be the node that represents material 401 or other nodes. A data 600 may specify the period of time. A data 700 may specify the sets of parameter values for the individual node (e.g., Xi) in network 500 at the discrete points in time of the period of time. A data 800 may specify the parameter values (e.g., ki(tm)) of the sets of parameter values for the individual node in network 500 at the discrete points in time of the period of time. denotes the nth parameter value for material i at time tj. Material i may be a material from list of previously synthesized materials 400. A data 900 may specify a status of discovery of material i (e.g., yi) if material i was first synthesized by the year 1950. Data 900 specifies whether material i was synthesized by the individual discrete points in time. The classifier model may be trained based on sets of parameter values for the individual node (e.g., Xi) and the status of discovery of material i (e.g., yi).

Figure 9:
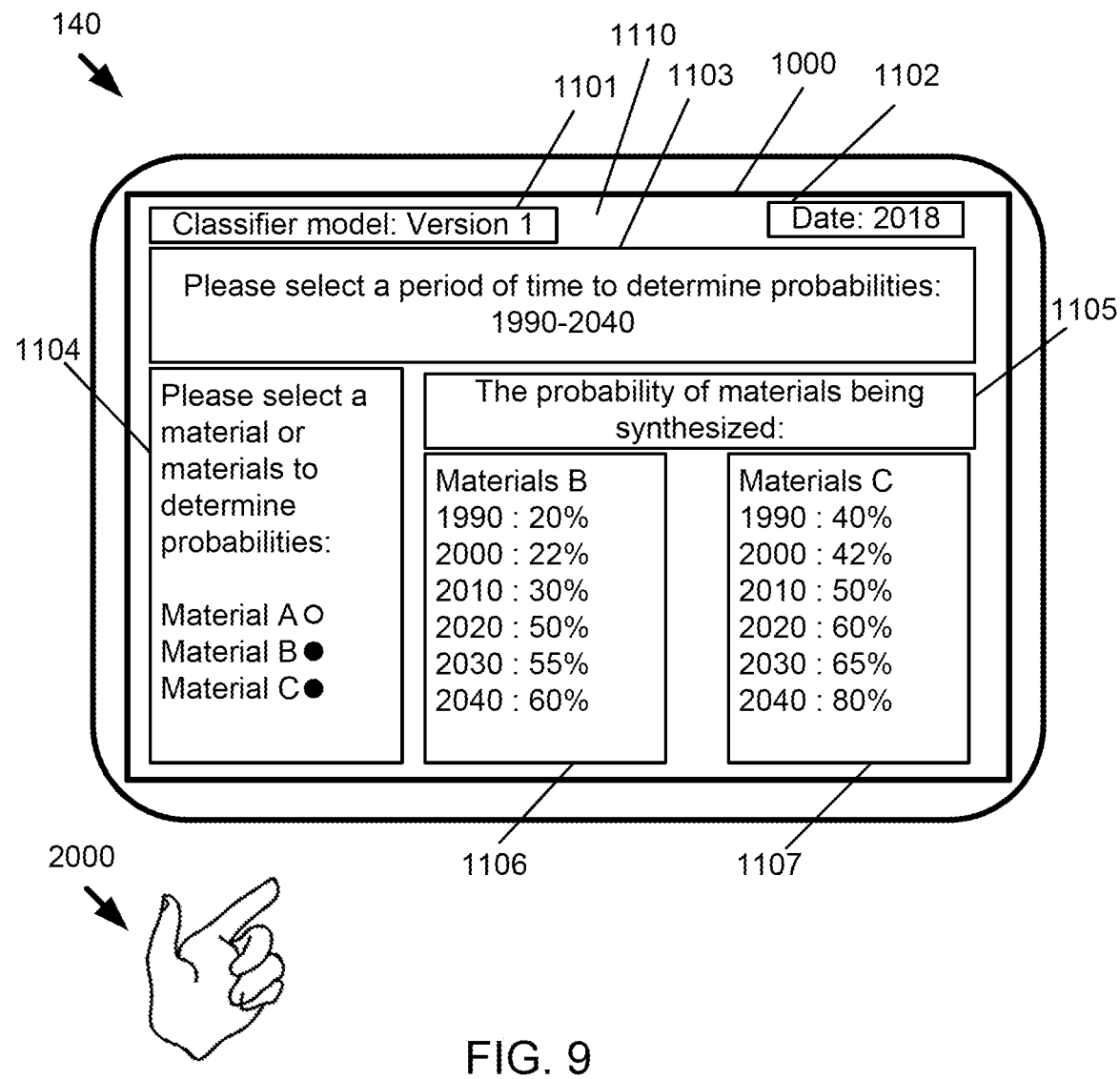
FIG. 9 illustrates an interface with probability information generated from a classifier model on a computing platform, in accordance with one or more implementations.

FIG. 9 illustrates an interface 1000 presented on a display of computing platform(s) 140. Interface 1000 includes one or more of a virtual space 1110, one or more virtual objects, and/or other components. The one or more virtual objects may include a first virtual object 1101, a second virtual object 1102, a third virtual object 1103, a fourth virtual object 1104, a fifth virtual object 1105, a sixth virtual object 1106, a seventh virtual object 1107, and/or other virtual objects. A user 2000 may interact with interface 1000. User may interact with the one or more virtual objects. In some implementations, first virtual object 1101 may effectuate presentation of a classifier model being used to generate probabilities for materials at discrete points in time over a period of time. User 2000 may change the classifier model user by selecting first virtual object 1101. User 2000 may retrain or modify the data used to train the classifier model by selecting first virtual object 1101. Second virtual object 1102 may effectuate presentation of the current time. The current time presented in FIG. 9 may be the year 2018. Third virtual object 1103 may effectuate presentation of a period of time to determine the probabilities. The period of time may be determined by user 2000 via user input in third virtual object 1103. Fourth virtual object 1104 may indicate materials probabilities are generated for. User 2000 may select the materials probabilities are generated for. Fifth virtual object 1105 may indicate the information being generated. Sixth virtual object 1106 may effectuate presentation of the generated probabilities for a material B at the discrete points in time of the period of time. Seventh virtual object 1107 may effectuate presentation of the generated probabilities for a material C at the discrete points in time of the period of time. In some implementations, user 2000 may determine the virtual objects presented on the topography of virtual space 1110. User 2000 may remove the virtual objects currently presented on the topography of virtual space 1110 in FIG. 9. User 2000 may include addition virtual objects to present on the topography of virtual space 1110 in FIG. 9. The additional virtual objects may effectuate addition information about the materials probabilities are generated for, the probabilities, the classifier model, and/or other information. User 2000 may add or remove the virtual objects may interacting with interface 1000.

Figure 10:
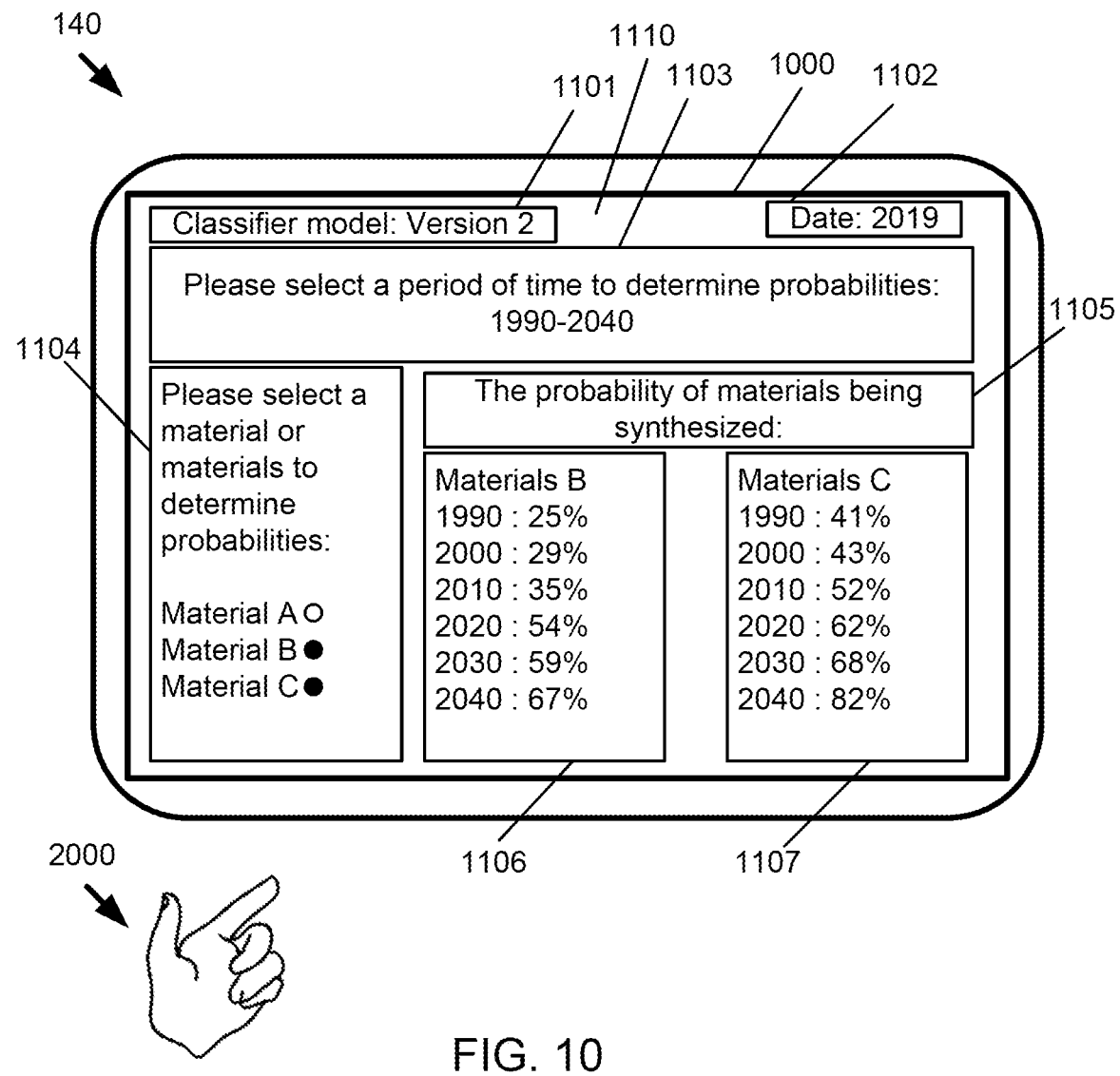
FIG. 10 illustrates the interface with the probability information generated from an updated classifier model on the computing platform, in accordance with one or more implementations.

FIG. 10 illustrates interface 1000 at a different time. The current time presented in FIG. 10 may be the year 2019. Second virtual object 1102 may indicate the current time presented in FIG. 10. One or more previously synthesized materials from the year 2018 may be synthesized by the year 2019. System 100 may update the classifier model used in the year 2018 based on the synthesized previously synthesized materials of the year 2019. First virtual object 1101 may effectuate presentation of the updated classifier model being used to generate probabilities for materials at discrete points in time over a period of time. Sixth virtual object 1106 may effectuate presentation of the generated probabilities for the material B at the discrete points in time of the period of time based on the updated classifier model. The probabilities for the material B being synthesized in the real world at the discrete points in time of the period of time may increase as a result of the synthesis of the previously synthesized materials. Seventh virtual object 1107 may effectuate presentation of the generated probabilities for the material C at the discrete points in time of the period of time based on the updated classifier model. The probabilities for the material C being synthesized in the real world at the discrete points in time of the period of time may increase as a result of the synthesis of the previously synthesized materials. In some implementations, user 2000 may interact with interface 1000 to view the synthesized previously synthesized materials. In some implementations, user 2000 may interact with interface 1000 to view the impact on the probabilities based on the synthesis of the previously synthesized materials.

Figure 11:
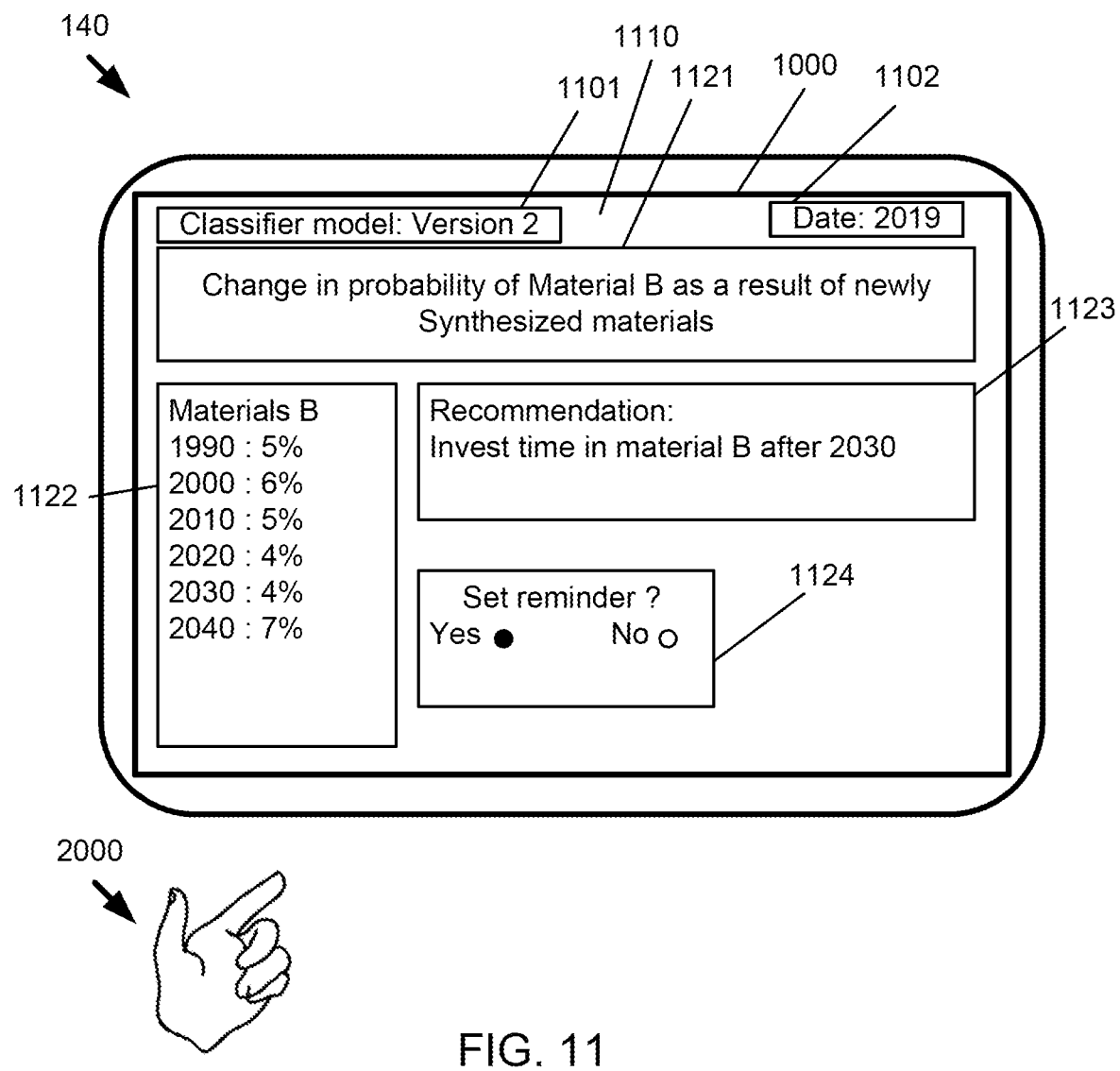
FIG. 11 illustrates the interface with information for a synthesized material based on newly acquired information, in accordance with one or more implementations.

FIG. 11 illustrates interface 1000 effectuating presentation of information characterizing the impact on the probabilities of synthesis of the material B based on the synthesis of the previously synthesized materials. A virtual object 1121 may indicate the information being presented on interface 1000. A virtual object 1122 may effectuate presentation of the impact on the probabilities of synthesis of the material B based on the synthesis of the previously synthesized materials. Virtual object 1122 may characterize a percentage change in the probabilities of synthesis of the material B at the discrete points in time. Virtual object 1123 may effectuate presentation of a notification for user 2000. The notification may provide user 2000 with a recommendation for synthesizing material B. Virtual object 1124 may effectuate presentation of an action for user 2000. The action may determine whether to remind user 2000 of material B at a later point in time. User 2000 may determine whether or not to get the reminder by interacting with virtual object 1124.

Figure 12:
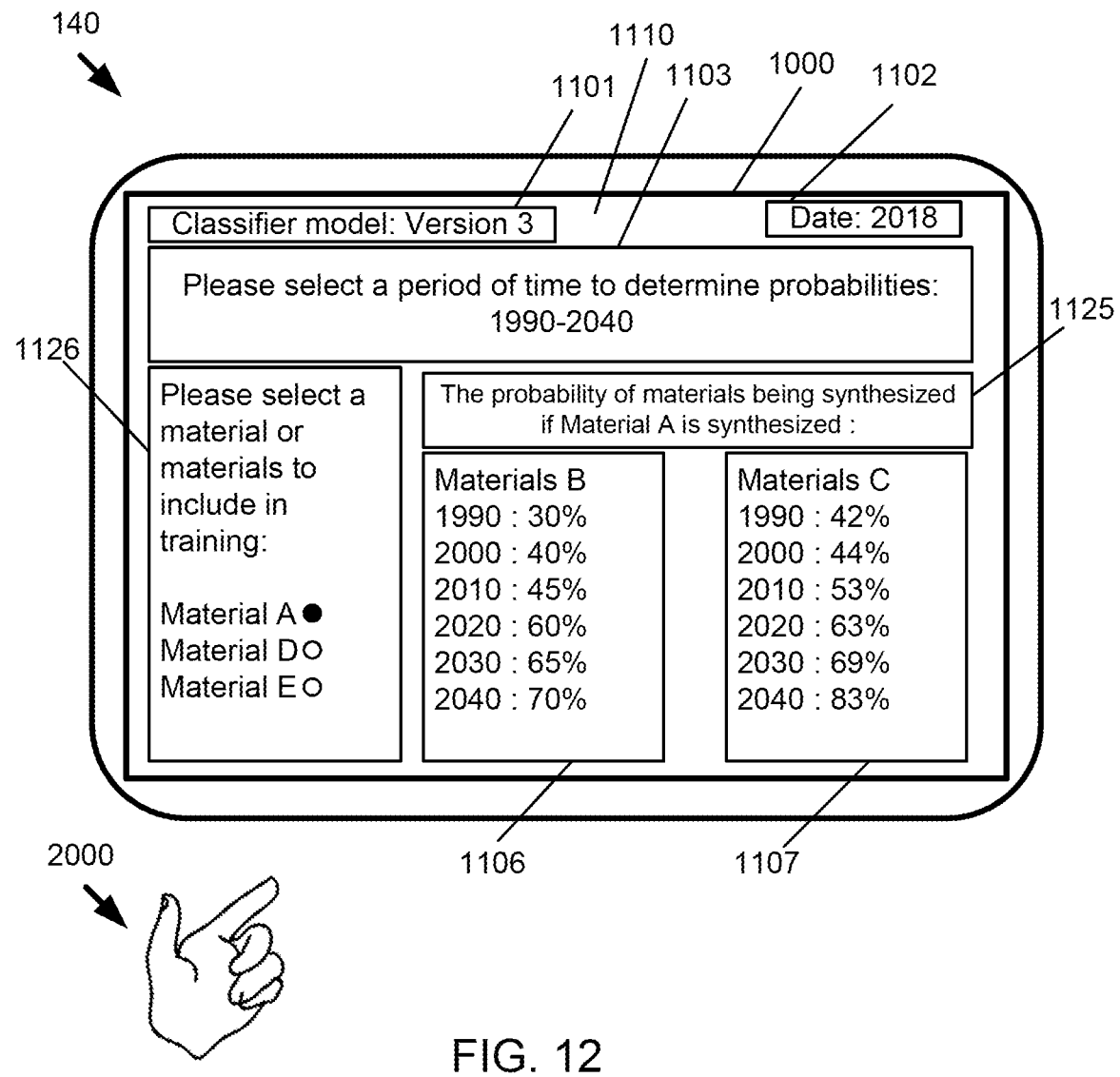
FIG. 12 illustrates the interface probability information generated from an altered classifier model on the computing platform, in accordance with one or more implementations.

FIG. 12 illustrates interface 1000 where the probabilities of materials are determined based on a material (e.g., a material A) being included in training or alteration of the classifier model. The Material A may be an unsynthesized material. The material may be included in the training of the classifier model to alter the probabilities generated by the classifier model. The material may be included in the training of the classifier model to determine a change in the probabilities of the materials being synthesized in the real world at the discrete points in time if Material A was synthesized. A virtual object 1125 may indicate the information presenting on interface 1000. A virtual object 1126 may indicate the material being included in training or alteration of the classifier model. User 2000 may determine the material being included in training or alteration of the classifier model. User 2000 may determine the material being included in training or alteration of the classifier model by interacting with virtual object 1126. Sixth virtual object 1106 may effectuate presentation of the generated probabilities for the material B at the discrete points in time of the period of time as a result of the Material A being included in training or alteration of the classifier model. Seventh virtual object 1107 may effectuate presentation of the generated probabilities for the material C at the discrete points in time of the period of time as a result of the Material A being included in training or alteration of the classifier model.

Figure 2:
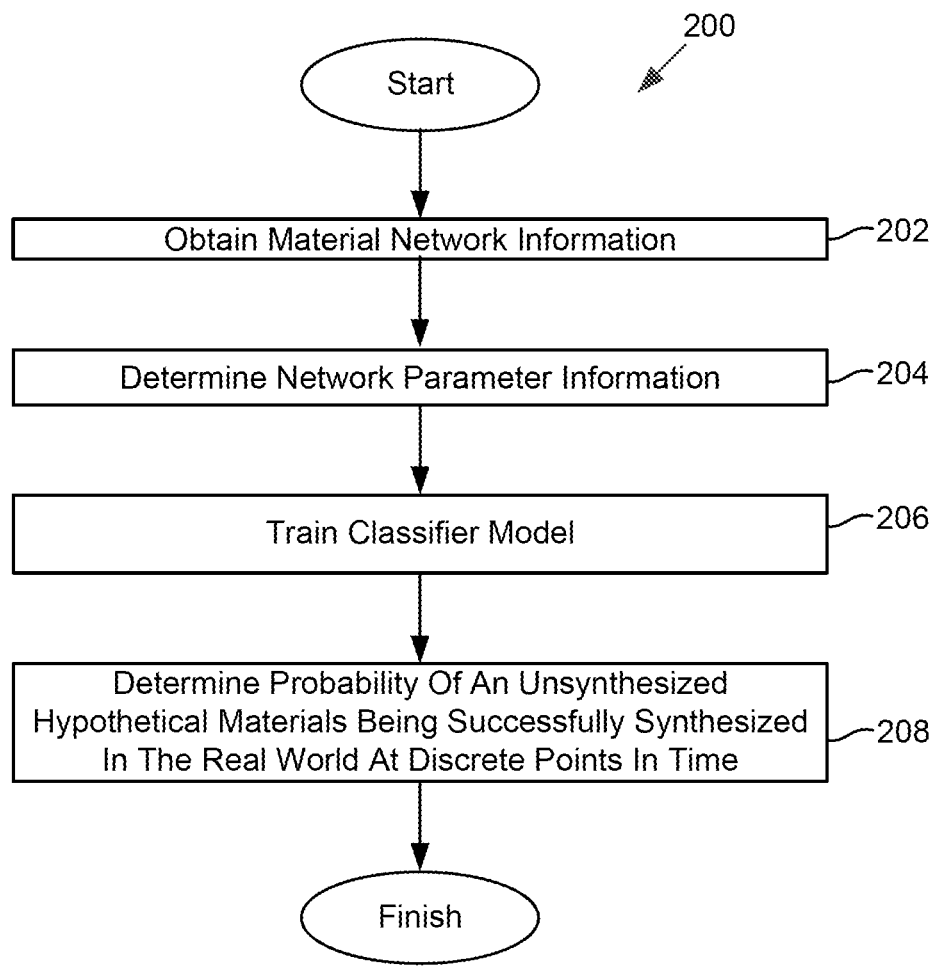
FIG. 2 illustrates a method for determining a probability of successful synthesis of a material as a function of time, in accordance with one or more implementations.

FIG. 2 illustrates the method 200, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below are not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, material network information may be obtained. The material network information may define a network for a set of previously synthesized materials. The material network information may include node information, edge information, discovery information, and/or other information. The node information may characterize previously synthesized materials represented by nodes in the network. The edge information may represent connections between the previously synthesized materials based on shared components between individual ones of the previously synthesized materials or other relationships (such as co-existence information from phase diagrams). The discovery information may define points in time the individual previously synthesized materials in the network were first synthesized in the real world. In some embodiments, operation 202 is performed by an information component the same as or similar to information component 106 (shown in FIG. 1 and described herein).

At an operation 204, network parameter information may be determined. The network parameter information may be for the network of the period of time. The network parameter information may specify sets of parameter values of individual nodes in the network at discrete points in time over a period of time. In some embodiments, operation 204 is performed by a determination component the same as or similar to determination component 108 (shown in FIG. 1 and described herein).

At an operation 206, a classifier model may be trained. The classifier model may be trained from the individual previously synthesized materials. The classifier model may be trained using the discovery information, the network parameter information, and/or other information. The classifier model may be trained to generate probabilities for materials being successfully synthesized in the real world at the individual discrete points in time. In some embodiments, operation 206 is performed by a training component the same as or similar to training component 110 (shown in FIG. 1 and described herein).

At an operation 208, probabilities of an unsynthesized hypothetical material being successfully synthesized in the real world at the individual discrete points in time may be determined. The probabilities of an unsynthesized hypothetical material being successfully synthesized in the real world at the individual discrete points in time may be determined by applying the classifier model. The probabilities of an unsynthesized hypothetical material being successfully synthesized in the real world at the individual discrete points in time may be determined by applying the classifier model to unsynthesized material information. The unsynthesized hypothetical material may define the unsynthesized hypothetical material. In some embodiments, operation 208 is performed by a prediction component the same as or similar to prediction component 112 (shown in FIG. 1 and described herein).

Figure 3:
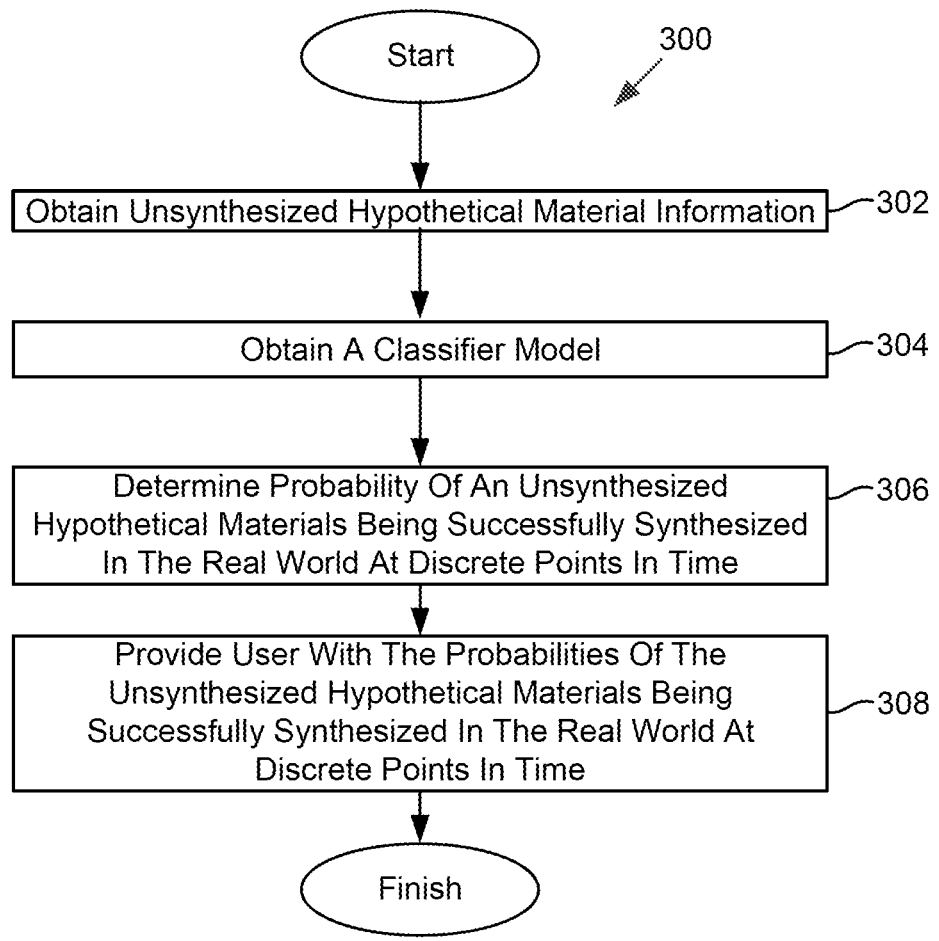
FIG. 3 illustrates a method for determining a probability of successful synthesis of a material as a function of time using a classifier model, in accordance with one or more implementations.

FIG. 3 illustrates the method 300, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below are not intended to be limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, unsynthesized hypothetical material information may be obtained. The unsynthesized hypothetical material information may define a set of parameter values for an unsynthesized hypothetical material. In some embodiments, operation 302 is performed by a prediction component the same as or similar to prediction component 112 (shown in FIG. 1 and described herein).

At an operation 304, a classifier model may be obtained. The classifier model may be obtained from a non-transient electronic storage. The non-transient electronic storage may store a trained classifier model, including the classifier model. The classifier model may be trained by a training data set. The training data set may include (i) sets of parameter values of a set of previously synthesized materials at the discrete points in time of the period of time and (ii) parameter values defining the discrete points in time the individual previously synthesized materials were synthesized in the real world. In some embodiments, operation 304 is performed by the prediction component the same as or similar to prediction component 112 (shown in FIG. 1 and described herein).

At an operation 306, probabilities of successful synthesis of the unsynthesized hypothetical material at the discrete points in time of the period of time may be determined. The probabilities may be defined by one or more values. The probabilities of successful synthesis of the unsynthesized hypothetical material at the discrete points in time of the period of time may be determined by applying the classifier model to the unsynthesized hypothetical material information. In some embodiments, operation 306 is performed by the prediction component the same as or similar to prediction component 112 (shown in FIG. 1 and described herein).

At an operation 308, the probabilities of successful synthesis of the unsynthesized hypothetical material at the discrete points in time of the period of time may be provided to a user. The probabilities of successful synthesis of the unsynthesized hypothetical material at the discrete points in time of the period of time may be provided to the user through a computing platform. In some embodiments, operation 308 is performed by the prediction component the same as or similar to prediction component 112 (shown in FIG. 1 and described herein).

Although the system(s) and/or method(s) of this disclosure have been described in detail for the purpose of illustration based on what is currently considered to be the most practical and/or preferred implementations, it is to be understood that such detail is solely for that purpose and/or that the disclosure is not limited to the disclosed implementations, but, on the contrary, is intended to cover modifications and/or equivalent arrangements that are within the spirit and/or scope of the appended claims. For example, it is to be understood that the present disclosure contemplates that, to the extent possible, one or more features of any implementation can be combined with one or more features of any other implementation.

What is claimed is:

1. A system configured to train a classifier model to determine a probability of successful synthesis of a material at one or more points in time, the system comprising:
one or more physical processors configured by machine-readable instructions to:
create a training set comprising material network information and network parameter information for a period of time, wherein:
the material network information defines a network for a set of previously synthesized materials and comprises discovery information defining points in time individual previously synthesized materials in the network were first synthesized, and
the network parameter information for the period of time specifies sets of parameter values of the previously synthesized materials; and
use the training set to train a classifier model from the individual previously synthesized materials using the discovery information and network parameter information to generate probabilities for materials being successfully synthesized at individual discrete points in time within the period of time.

2. The system of claim 1, wherein the discovery information specifies whether individual previously synthesized materials were synthesized at given points in time over the period of time.

3. The system of claim 1, wherein:
the material network information includes node information characterizing previously synthesized materials represented by nodes in the network; and
the network at discrete points in time include a first point in time, and the network at the first point in time is characterized by the material network information for the nodes in the network representing previously synthesized materials that were synthesized prior to the first point in time.

4. The system of claim 1, wherein a set of parameter values includes values for at least one of degree parameter, degree centrality parameter, eigenvector centrality parameter, mean shortest path parameter, mean degree of neighbors parameter, and clustering coefficient parameter.

5. The system of claim 1, wherein the one or more physical processors are further configured by machine-readable instructions to:
update the training set to further comprise synthesis information, wherein the synthesis information defines one or more synthesized materials not included in the network with the previously synthesized materials; and
re-train the classifier model using the updated training set to generate probabilities for materials being successfully synthesized at the individual discrete points in time within the time period.

6. The system of claim 1, wherein the trained classifier model is stored in a non-transient electronic storage.

7. A method for training a classifier model to determine a probability of successful synthesis of a material at one or more points in time, the method comprising:
creating a training set comprising material network information and network parameter information for a period of time, wherein:
the material network information defines a network for a set of previously synthesized materials and comprises discovery information defining points in time individual previously synthesized materials in the network were first synthesized, and
the network parameter information for the period of time specifies sets of parameter values of the previously synthesized materials; and
using the training set to train a classifier model to generate probabilities for materials being successfully synthesized at individual discrete points in time within the period of time.

8. The method of claim 7, wherein the discovery information specifies whether individual previously synthesized materials were synthesized at given points in time over the period of time.

9. The method of claim 7, wherein:
the material network information includes node information characterizing previously synthesized materials represented by nodes in the network; and
the network at discrete points in time include a first point in time, and the network at the first point in time is characterized by the material network information for the nodes in the network representing previously synthesized materials that were synthesized prior to the first point in time.

10. The method of claim 7, wherein a set of parameter values includes values for at least one of degree parameter, degree centrality parameter, eigenvector centrality parameter, mean shortest path parameter, mean degree of neighbors parameter, and clustering coefficient parameter.

11. The method of claim 7, further comprising:
updating the training set to further comprise synthesis information, wherein the synthesis information defines one or more synthesized materials not included in the network with the previously synthesized materials; and
re-training the classifier model using the updated training set to generate probabilities for materials being successfully synthesized at the individual discrete points in time within the time period.

12. The method of claim 7, wherein the trained classifier model is stored in a non-transient electronic storage.

* * * * *